(12) United States Patent
Mitsuhashi

(10) Patent No.: US 10,932,648 B2
(45) Date of Patent: Mar. 2, 2021

(54) IMAGE PROCESSING APPARATUS, IMAGE PROCESSING METHOD, AND COMPUTER-READABLE RECORDING MEDIUM

(71) Applicant: OLYMPUS CORPORATION, Tokyo (JP)

(72) Inventor: Kei Mitsuhashi, Nishitokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 686 days.

(21) Appl. No.: 15/592,845

(22) Filed: May 11, 2017

(65) Prior Publication Data
US 2017/0245736 A1 Aug. 31, 2017

Related U.S. Application Data

(63) Continuation of application No. PCT/JP2016/059257, filed on Mar. 23, 2016.

(30) Foreign Application Priority Data

Jul. 28, 2015 (JP) .............................. JP2015-148491

(51) Int. Cl.
*A61B 1/00* (2006.01)
*A61B 1/04* (2006.01)

(52) U.S. Cl.
CPC ............ *A61B 1/00009* (2013.01); *A61B 1/00* (2013.01); *A61B 1/00016* (2013.01); *A61B 1/041* (2013.01); *A61B 1/04* (2013.01)

(58) Field of Classification Search
CPC ....... A61B 1/00009; A61B 1/00; A61B 1/041; A61B 1/00016; A61B 1/04; A61B 5/073
See application file for complete search history.

(56) References Cited

U.S. PATENT DOCUMENTS 8,328,712 B2  12/2012  Nishiyama et al.
2006/0106318 A1*  5/2006  Davidson ............. A61B 1/0005
                                                            600/476

(Continued)

FOREIGN PATENT DOCUMENTS

JP    2007-236700 A    9/2007
JP    4865912 B2    11/2011

(Continued)

OTHER PUBLICATIONS

International Search Report dated Jun. 28, 2016 issued in PCT/JP2016/059257.

(Continued)

*Primary Examiner* — Timothy J Neal
(74) *Attorney, Agent, or Firm* — Scully, Scott, Murphy & Presser, P.C.

(57) ABSTRACT

An image processing apparatus includes a processor comprising hardware. The processor is configured to: acquire a movement amount of a capsule endoscope in a movement direction of the capsule endoscope, based on information transmitted from the capsule endoscope including an imaging sensor; and determine whether to associate a first image captured by the imaging sensor with a second image, which is captured by the imaging sensor and is captured at a time different from a time in which the imaging sensor captures the first image, based on an imaging distance of the imaging sensor in the movement direction, and the movement amount.

12 Claims, 17 Drawing Sheets

(56) References Cited

U.S. PATENT DOCUMENTS

| | | | |
|---|---|---|---|
| 2008/0242926 A1* | 10/2008 | Nishino | A61B 1/041 600/109 |
| 2009/0043157 A1* | 2/2009 | Hirakawa | A61B 5/06 600/109 |
| 2011/0218397 A1* | 9/2011 | Nishiyama | A61B 1/00009 600/109 |
| 2013/0002842 A1* | 1/2013 | Das | H04N 7/18 348/65 |
| 2013/0217962 A1 | 8/2013 | Date et al. | |
| 2015/0221116 A1 | 8/2015 | Wu et al. | |
| 2015/0297067 A1* | 10/2015 | Yanagidate | A61B 5/06 600/109 |

FOREIGN PATENT DOCUMENTS

| | | |
|---|---|---|
| JP | 4891646 B2 | 12/2011 |
| WO | WO 2013/015104 A1 | 1/2013 |
| WO | WO 2014/193670 A2 | 12/2014 |
| WO | WO-2014193670 A2 * | 12/2014 |

OTHER PUBLICATIONS

English Abstract only of JP 2007-282794 dated Nov. 1, 2007.
English Abstract only of WO 2010/109726 A1 dated Sep. 30, 2010.

* cited by examiner

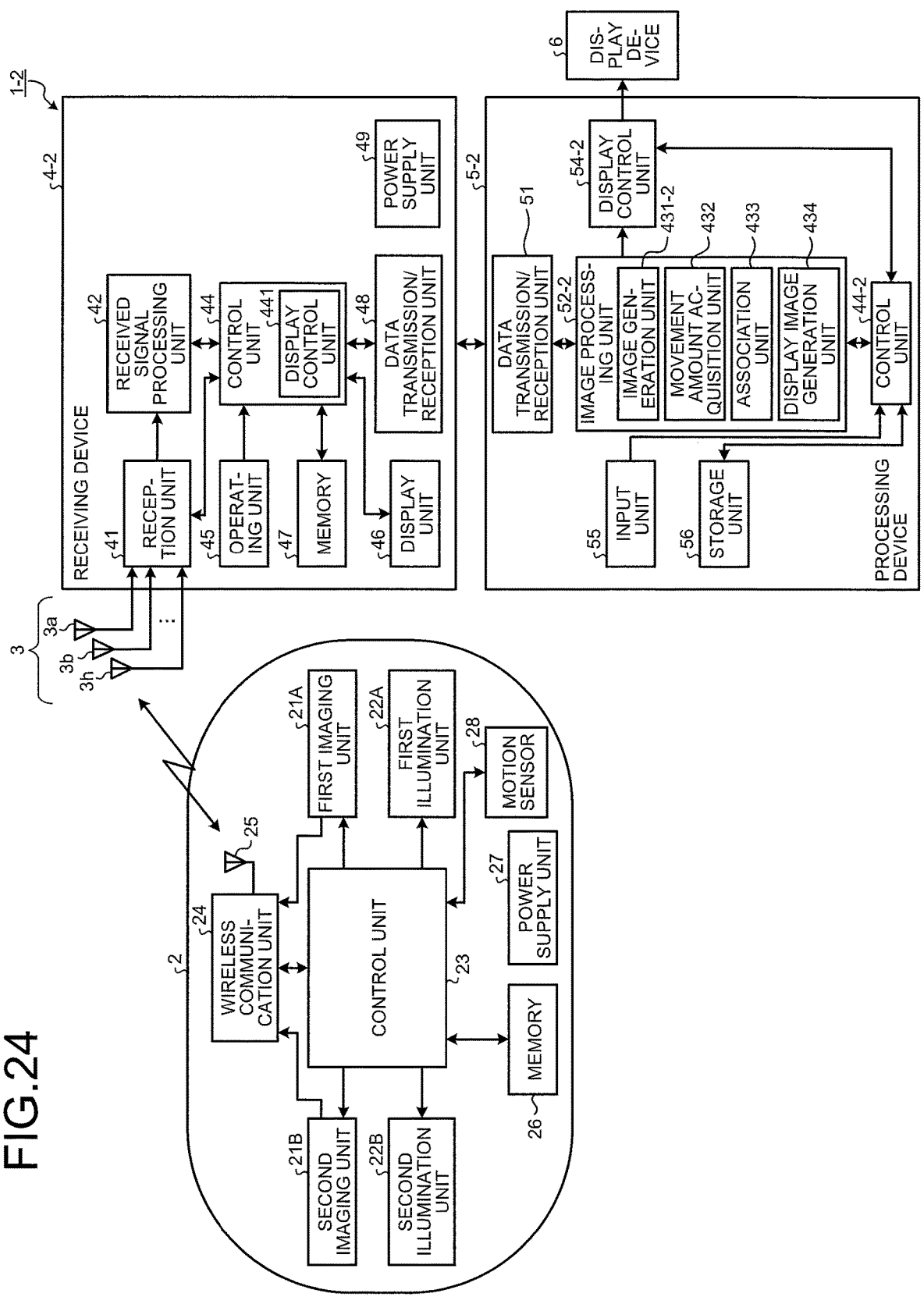

IMAGE PROCESSING APPARATUS, IMAGE PROCESSING METHOD, AND COMPUTER-READABLE RECORDING MEDIUM

CROSS-REFERENCE TO RELATED APPLICATIONS

This application is a continuation of PCT international application Ser. No. PCT/JP2016/059257 filed on Mar. 23, 2016 which designates the United States, incorporated herein by reference, and which claims the benefit of priority from Japanese Patent Application No. 2015-148491, filed on Jul. 28, 2015, incorporated herein by reference.

BACKGROUND

1. Technical Field

The disclosure relates to an image processing apparatus, an image processing method, and a computer-readable recording medium which process an image captured by an imaging unit of a capsule endoscope.

2. Related Art

In the field of endoscopes, capsule endoscopes have been developed which are formed in a size small enough to be introduced into a digestive tract of a subject such a patient. A capsule endoscope is a device having a capsule-shaped casing including an imaging function and a wireless communication function therein, the capsule endoscope swallowed from a mouth of a subject sequentially images inside an organ of the subject while moving in a digestive tract with peristaltic motion or the like to acquire images, and wirelessly transmits the images to a receiving device outside the subject. The receiving device sequentially receives the images transmitted from the capsule endoscope, and causes a recording medium to sequentially record the images. An image display device captures the images recorded in the recording medium, performs predetermined image processing on the images, and then plays back the images as in-vivo images while switching the images frame by frame (frame playback). A physician or the like as an operator diagnoses the in-vivo images played back on the image display device to diagnose the subject.

In recent years, so-called pantoscopic capsule endoscopes have been proposed which include a plurality of imaging units capturing images in different directions. These pantoscopic capsule endoscopes capturing the images in different directions allows multidirectional imaging inside a subject. When a binocular capsule endoscope is used, the number of internal images of the subject is substantially twice that of a monocular capsule endoscope. Thus, in order to increase the efficiency in observation diagnosis, simultaneous display of images showing a spatially continuous area between the images has been desired.

In order to meet this request, there has been proposed a technique for synchronously displaying images captured at a predetermined time interval, selected from images of a first image group captured by a first imaging unit of a capsule endoscope, and images of a second image group captured by a second imaging unit (e.g., see JP 4891646 B2), and a technique for calculating a similarity between sequential images selected from images of a first image group and from images of a second image group to synchronously display similar images (e.g., see JP 4865912 B2).

SUMMARY

In some embodiments, an image processing apparatus includes a processor comprising hardware. The processor is configured to: acquire a movement amount of a capsule endoscope in a movement direction of the capsule endoscope, based on information transmitted from the capsule endoscope including an imaging sensor; and determine whether to associate a first image captured by the imaging sensor with a second image, which is captured by the imaging sensor and is captured at a time different from a time in which the imaging sensor captures the first image, based on an imaging distance of the imaging sensor in the movement direction, and the movement amount.

In some embodiments, an image processing method performed by an image processing apparatus processing an image captured by an imaging sensor of a capsule endoscope is provide. The method includes: acquiring a movement amount of the capsule endoscope in a movement direction of the capsule endoscope; and determining whether to associate a first image captured by the imaging sensor, with a second image captured by the imaging sensor and is captured at a time different from a time in which the imaging sensor captures the first image, based on an imaging distance of the imaging sensor in the movement direction, and the movement amount.

In some embodiments, a non-transitory computer-readable recording medium recording an image processing program is provided. The program causes an image processing apparatus processing an image captured by an imaging sensor of a capsule endoscope to perform: acquiring a movement amount of the capsule endoscope in a movement direction of the capsule endoscope; and determining whether to associate a first image captured by the imaging sensor, with a second image captured by the imaging sensor and is captured at a time different from a time in which the imaging sensor captures the first image, based on an imaging distance of the imaging sensor in the movement direction, and the movement amount.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 24 is a block diagram illustrating another configuration of the capsule endoscope system according to the fourth modification of the embodiment.

DETAILED DESCRIPTION

An endoscope system using a medical capsule endoscope according to embodiments of the disclosure will be described below. It should be understood that the disclosure is not limited to these embodiments. Further, in the description of the drawings, the same portions are denoted by the same reference signs. It should be noted that each of the drawings is schematically illustrated, and a relationship between the thickness and the width of each member, the proportion or the like of each member may be different from those of actual one. Further, the dimensional relationship or proportion may be partially different between the drawings.

Embodiment

Figure 1:
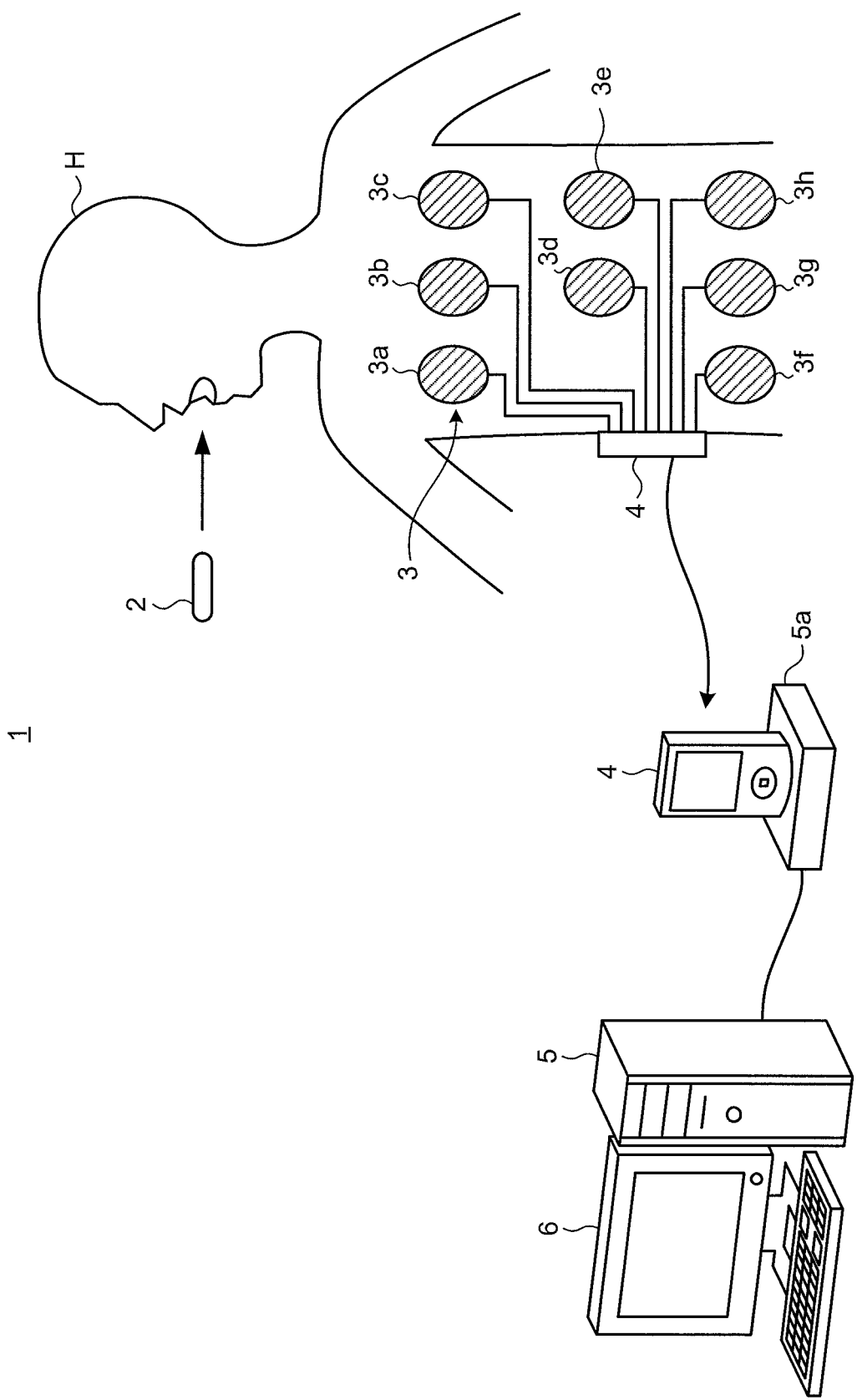
FIG. 1 is a schematic view of a schematic configuration of an endoscope system according to an embodiment of the disclosure.

FIG. 1 is a schematic view of a schematic configuration of the endoscope system according to an embodiment of the disclosure. As illustrated in FIG. 1, a capsule endoscope system 1 according to the embodiment includes a capsule endoscope 2 introduced into a subject H, imaging inside the subject H, acquiring an imaging signal, and transmitting the imaging signal superimposed on a wireless signal, a receiving device 4 receiving the wireless signal transmitted from the capsule endoscope 2, through a receiving antenna unit 3 including a plurality of receiving antennas 3a to 3h mounted to the subject H, and a processing device 5 capturing the imaging signal captured by the capsule endoscope 2, from the receiving device 4, through a cradle 5a, processing the imaging signal, and generating an in-vivo image of the subject H. The image generated by the processing device 5 is for example output from a display device 6 to be displayed thereon. Furthermore, the receiving device 4 includes a display unit, generates the in-vivo images of the subject H from the imaging signals captured by the capsule endoscope 2, and synchronously displays two images showing a spatially continuous area between the two images, on the display unit.

Figure 2:
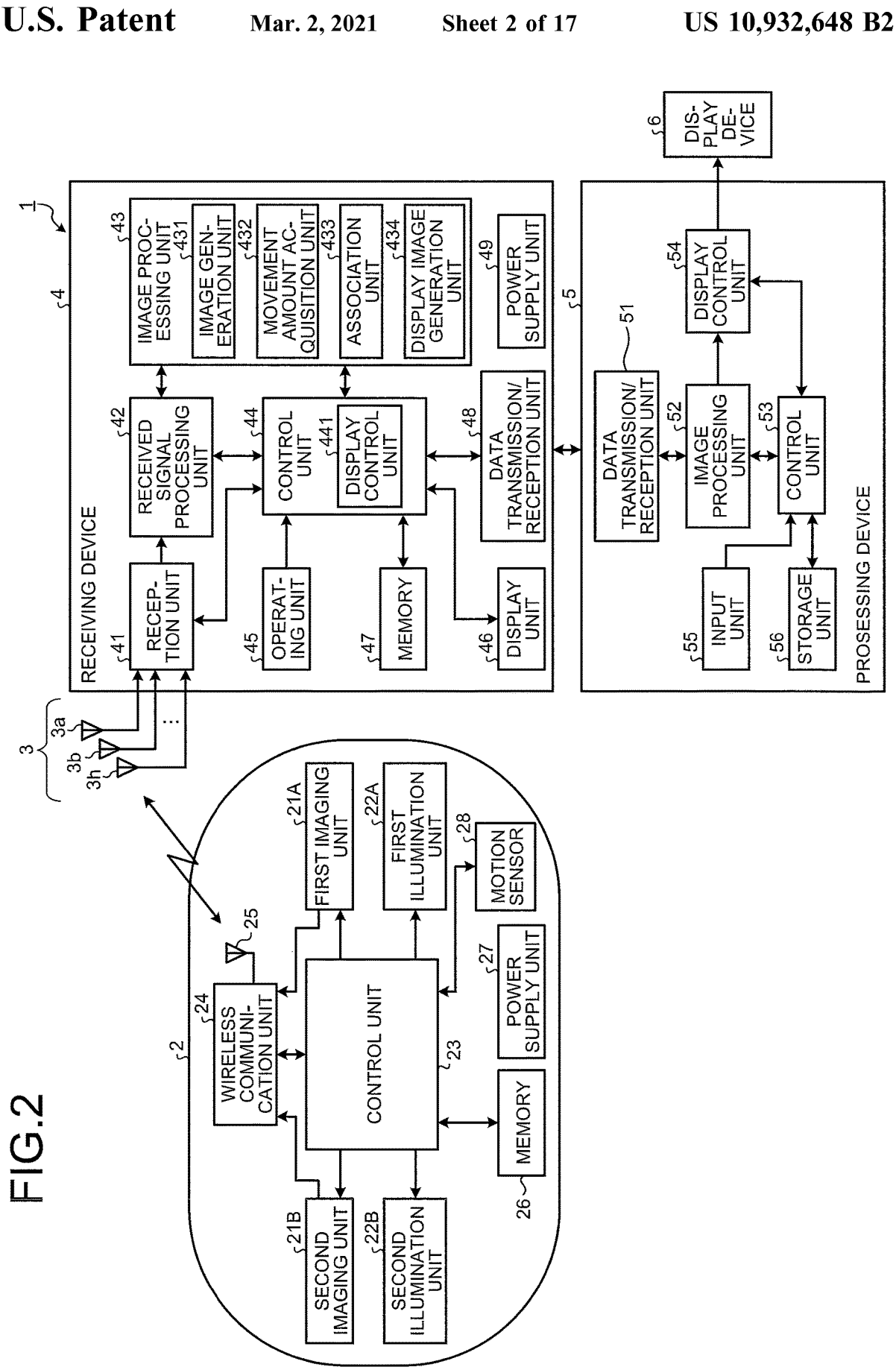
FIG. 2 is a block diagram illustrating a configuration of a capsule endoscope system illustrated in FIG. 1.
Figure 3:
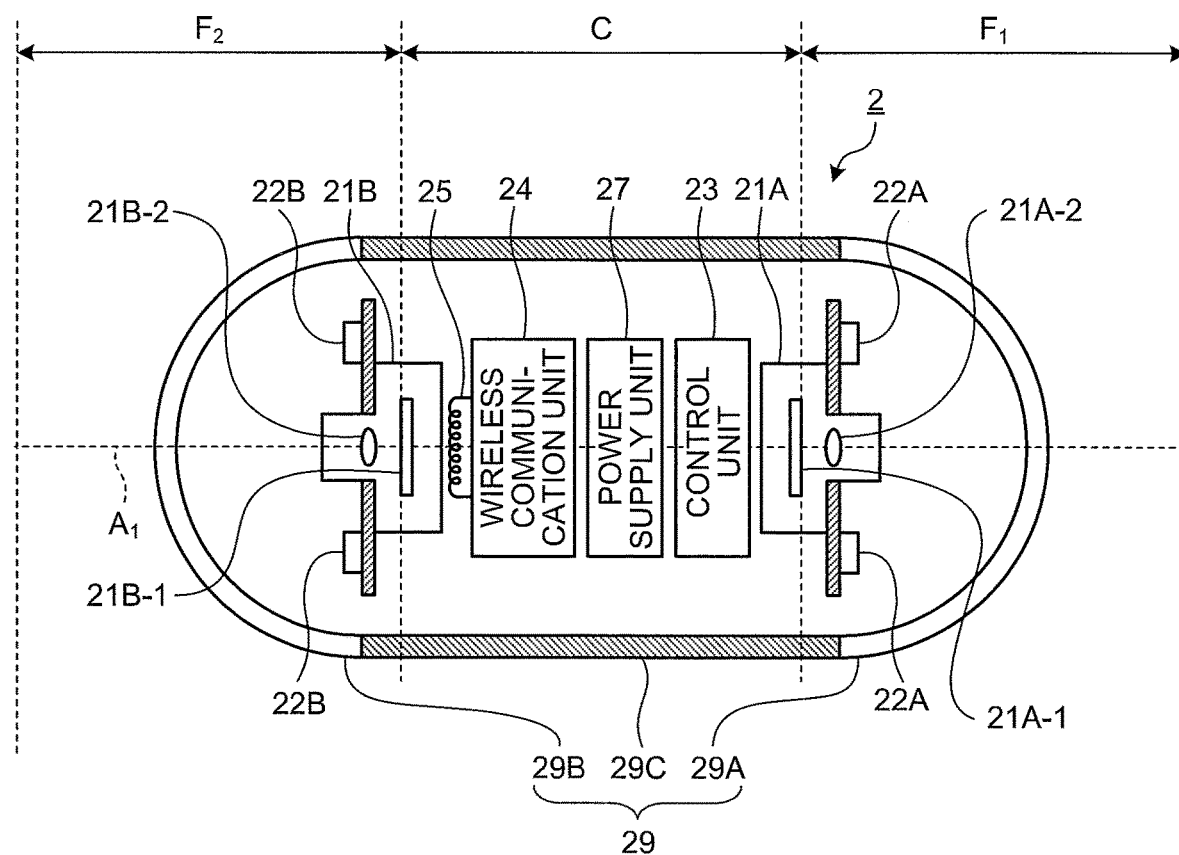
FIG. 3 is a schematic cross-sectional view illustrating an exemplary configuration of a capsule endoscope illustrated in FIG. 1.

FIG. 2 is a block diagram illustrating a configuration of the capsule endoscope system 1. FIG. 3 is a schematic cross-sectional view illustrating an exemplary configuration of the capsule endoscope 2 illustrated in FIG. 1. The capsule endoscope 2 includes a first imaging unit 21A, a second imaging unit 21B, a first illumination unit 22A, a second illumination unit 22B, a control unit 23, a wireless communication unit 24, an antenna 25, a memory 26, a power supply unit 27, and a motion sensor 28. The capsule endoscope 2 is a device having various built-in components such as an imaging element in a capsule-shaped casing 29 (see FIG. 3) having a size small enough to be swallowed by the subject H.

The first imaging unit 21A and the second imaging unit 21B respectively include for example, imaging elements 21A-1 and 21B-1 each generating the imaging signal representing the inside of the subject H from an optical image formed on a light receiving surface, and outputting the imaging signal, and optical systems 21A-2 and 21B-2, such as objective lenses, respectively disposed facing the light receiving surfaces of the imaging elements 21A-1 and 21B-1. Each of the imaging elements 21A-1 and 21B-1 includes a CCD imaging element or a CMOS imaging element, has a plurality of pixels receiving light from the subject H, which is arranged in a matrix, performs photoelectric conversion on light received by the pixels, and generates the imaging signal.

The first imaging unit 21A and the second imaging unit 21B capture images in different imaging directions. The capsule endoscope 2 is a binocular capsule medical device performing imaging of forward and backward areas from the capsule endoscope 2 in the major axis direction, and in the embodiment, a description will be given of an exemplary configuration in which the first imaging unit 21A and the second imaging unit 21B have an optical axis $A_1$ substantially parallel with or substantially coincide with a longitudinal axis of the capsule endoscope 2.

Furthermore, the first imaging unit 21A and the second imaging unit 21B respectively have opposite imaging directions. When a movement direction of the capsule endoscope 2 coincides with the optical axis $A_1$, $F_1$ shown in FIG. 3 represents an observation depth (first observation depth) of the first imaging unit 21A, and a distance between both ends of an effective imaging area of the first imaging unit 21A along the optical axis $A_1$. The effective imaging area is an area providing a predetermined brightness and a predetermined resolving power for an image captured by the imaging unit. In FIG. 3, $F_2$ represents an observation depth (second observation depth) of the second imaging unit 21B, and a distance between both ends of an effective imaging area of the second imaging unit 21B along the optical axis $A_1$. In FIG. 3, C represents a distance between the light receiving surface of the imaging element 21A-1 and the light receiving surface of the imaging element 21B-1. Any of $F_1$, $F_2$, and C is a known value corresponding to the type of the capsule endoscope 2, and is stored in the receiving device 4 and the processing device 5 described later.

Figure 4:
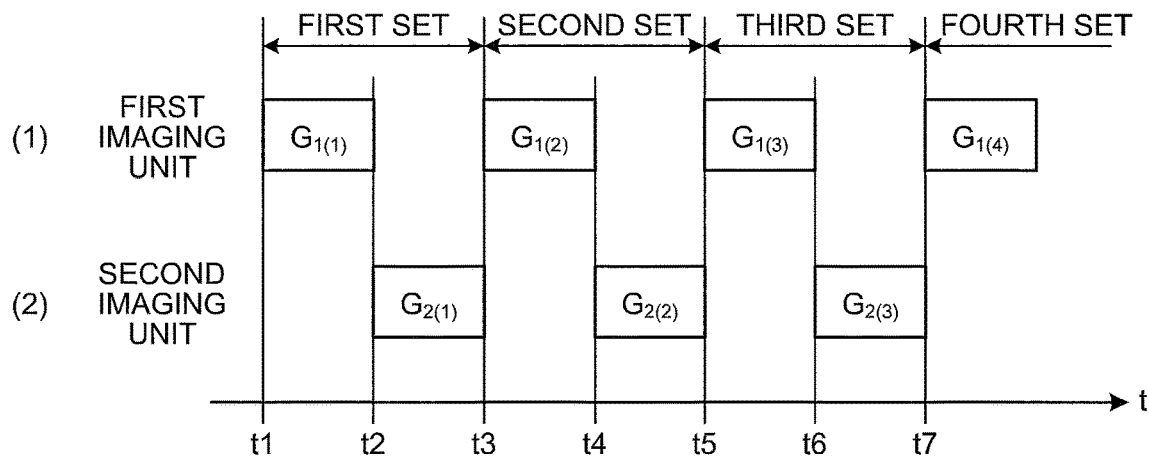
FIG. 4 is a diagram illustrating processing timing in imaging processing by a first imaging unit and a second imaging unit illustrated in FIG. 2.

FIG. 4 is a diagram illustrating processing timing in imaging processing by the first imaging unit 21A and the second imaging unit 21B. As illustrated in (1) of FIG. 4 and (2) of FIG. 4, the first imaging unit 21A and the second imaging unit 21B alternately perform the imaging processing. For example, the first imaging unit 21A performs imaging processing at imaging start time t1, and the second imaging unit 21B performs imaging processing at imaging start time t2. An image $G_{1(1)}$ based on an imaging signal captured at the imaging start time t1 by the first imaging unit 21A, and an image $G_{2(1)}$ based on the imaging signal captured at the imaging start time t2 by the second imaging unit 21B are associated with each other as the first set of images. Similarly, for the second set of images, an image $G_{1(2)}$ based on an imaging signal captured at imaging start time t3 by the first imaging unit 21A, and an image $G_{2(2)}$ based on an imaging signal captured at imaging start time t4 by the second imaging unit 21B are associated with each other, and for the third set of images, an image $G_{1(3)}$ based on an imaging signal captured at imaging start time t5 by the first imaging unit 21A, and an image $G_{2(3)}$ based on an imaging signal captured at imaging start time t6 by the second imaging unit 21B are associated with each other. Imaging is similarly performed on images subsequent to an image $G_{1(4)}$ of the fourth set.

The first illumination unit 22A and the second illumination unit 22B each include white LED or the like generating white light as illumination light.

The control unit 23 controls operation processes of the component parts of the capsule endoscope 2. For example, when the first imaging unit 21A and the second imaging unit 21B alternately perform imaging processing, the control unit 23 controls the first imaging unit 21A and the second imaging unit 21B to alternately expose and read the imaging elements 21A-1 and 21B-1, and controls the first illumination unit 22A and the second illumination unit 22B to emit illumination light according to exposure timing of corresponding imaging units.

The wireless communication unit 24 processes imaging signals output from the first imaging unit 21A and the second imaging unit 21B. The wireless communication unit 24 performs A/D conversion and predetermined signal processing on each of the imaging signals output from the first imaging unit 21A and the second imaging unit 21B to acquire a digital imaging signal, and superimposes the digital imaging signal on the wireless signal, together with related information to be transmitted to the outside from the antenna 25. The related information includes identification information (e.g., serial number) assigned to identify individual capsule endoscope 2, identification information identifying whether any of the first imaging unit 21A and the second imaging unit 21B performs the imaging, a detection signal detected by the motion sensor 28 described later, and the like.

The memory 26 stores execution programs and control programs for execution of various operations by the control unit 23. Furthermore, the memory 26 may temporarily store the imaging signal or the like on which the signal processing is performed by the wireless communication unit 24.

The power supply unit 27 includes a battery including a button battery or the like, a power supply circuit for boosting or the like of power from the battery, and a power supply switch switching the power supply unit 27 between an on state and an off state, and the power supply unit 27 supplies power to each unit in the capsule endoscope 2, after the power supply switch is turned on. Note that the power supply switch includes for example a reed switch switched between an on state and an off state by an external magnetic force, and is switched to the on state by application of a magnetic force to the capsule endoscope 2 from outside, before use of the capsule endoscope 2 (before swallowed by the subject H).

The motion sensor 28 is a sensor, such as an acceleration sensor, acquiring a movement amount of the capsule endoscope 2. The motion sensor 28 is disposed near the center portion of the capsule endoscope 2, detects acceleration in three axial directions applied to the casing 29, and outputs the detection signal. Furthermore, a positional relationship between the motion sensor 28, the first imaging unit 21A, and the second imaging unit 21B is previously set and stored. Thus, a posture of the capsule endoscope 2 can be determined on the basis of the detection signal from the motion sensor 28 to identify a positional relationship between the first imaging unit 21A and the second imaging unit 21B (upper/lower, back side/front side, or the like).

The casing 29 is an outer casing formed in a size small enough to be introduced into an organ of the subject H, and is achieved by closing opening ends on both sides of a cylindrical casing 29C by domed casings 29A and 29B. The domed casings 29A and 29B are dome shaped optical members transparent to light of a predetermined wavelength band, such as visible light. The cylindrical casing 29C is a colored casing substantially opaque to visible light. As illustrated in FIG. 3, the casing 29 including such a cylindrical casing 29C and domed casings 29A and 29B liquid-tightly encapsulates the component parts of the capsule endoscope 2.

Such a capsule endoscope 2 sequentially images a portion of a living body (esophagus, stomach, small intestine, large intestine, or the like) at predetermined intervals (e.g., 0.5 second intervals), while moving in a digestive tract of the subject H with peristaltic motion or the like of an organ, after the capsule endoscope 2 is swallowed by the subject H. Then, the imaging signals and the related information acquired during this imaging operation are wirelessly transmitted to the receiving device 4 sequentially.

The receiving device 4 includes a reception unit 41, a received signal processing unit 42, an image processing unit 43, a control unit 44, an operating unit 45, a display unit 46, a memory 47, a data transmission/reception unit 48, and a power supply unit 49 supplying power to these units.

The reception unit 41 receives the imaging signals and the related information wirelessly transmitted from the capsule endoscope 2, through the receiving antenna unit 3 having the plurality of receiving antennas 3a to 3h (eight receiving antennas in FIG. 1). Each of the receiving antennas 3a to 3h employs for example a loop antenna or a dipole antenna, and is disposed at a predetermined position on an outer body surface of the subject H.

The received signal processing unit 42 performs predetermined signal processing on the imaging signal received by the reception unit 41. The received signal processing unit 42 includes a processor such as a CPU. The received signal processing unit 42 acquires each imaging signal superimposed on a signal received by the reception unit 41, the identification information identifying whether any of the first imaging unit 21A and the second imaging unit 21B captures the imaging signal, and the related information including the detection signal of acceleration or the like detected by the motion sensor 28, and the like. The imaging signal, the identification information, and the detection signal acquired by the received signal processing unit 42 are output to the image processing unit 43.

The image processing unit 43 performs predetermined image processing on the imaging signal input from the received signal processing unit 42, and generates an image to be displayed on the display unit 46. The image processing unit 43 includes a processor such as a CPU. The image processing unit 43 includes an image generation unit 431, a movement amount acquisition unit 432, an association unit 433, and a display image generation unit 434.

The image generation unit 431 generates an image on the basis of the imaging signal input from the received signal processing unit 42. The image generation unit 431 performs, on the input imaging signal, optical black subtraction (OB) processing, demosaicing processing, density conversion (gamma conversion or the like) processing, smoothing (noise removal or the like) processing, white balance (WB) adjustment processing, synchronization processing, electronic zooming, edge enhancement processing, and the like corresponding to the type of the first imaging unit 21A, and outputs the generated image. The image generation unit 431 associates the generated image with information identifying whether any of the first imaging unit 21A and the second imaging unit 21B performs the imaging.

The movement amount acquisition unit 432 acquires the movement amount of the capsule endoscope 2 in the movement direction of the capsule endoscope 2, on the basis of the detection signal of the acceleration or the like detected by the motion sensor 28. On the basis of the acceleration detected by the motion sensor 28 at a time in which the first imaging unit 21A captures each of two imaging signals, the movement amount acquisition unit 432 acquires the movement amount of the capsule endoscope 2 moved in the movement direction while the first imaging unit 21A captures these two imaging signals. Furthermore, the movement amount acquisition unit 432 may perform image processing to acquire the movement amount of the capsule endoscope 2 in the movement direction. In this configuration, two images captured by a single imaging unit are used to calculate the movement amount. For example, two images captured by the first imaging unit 21A are processed to acquire the movement amount of the capsule endoscope 2 moved in the movement direction during a time in which the first imaging unit 21A captures imaging signals corresponding to these two images. As a matter of course, the imaging signals captured by the second imaging unit 21B may be used.

The association unit 433 associates a first image captured by an imaging unit with a second image captured with an effective imaging area continued from an effective imaging area of the imaging unit upon capturing the first image, on the basis of at least an imaging distance of the imaging unit in the movement direction and the movement amount of the capsule endoscope 2 acquired by the movement amount acquisition unit 432. The association unit 433 associates the second image with the first image based on the imaging signal captured by the first imaging unit 21A. The second image is an image selected from an image group based on the imaging signals captured by the second imaging unit 21B, and captured with the effective imaging area continued from the effective imaging area of the first imaging unit 21A upon capturing the first image. For a candidate image captured by the second imaging unit 21B which is a candidate for the second image, the association unit 433 calculates a first distance along the movement direction between a position of the first imaging unit 21A upon capturing the first image and a position of the second imaging unit 21B upon capturing the candidate image, on the basis of the movement amount of the capsule endoscope 2 in the movement direction, acquired by the movement amount acquisition unit 432, compares the calculated first distance and the imaging distance with each other, and determines whether to associate the candidate image as the second image, with the first image. The imaging distance is a distance between both ends of an effective imaging area along the movement direction, in the effective imaging area in which the predetermined brightness and the predetermined resolving power is provided for an image captured by an imaging unit. In the capsule endoscope 2, the imaging distance is the sum of the observation depth $F_1$ of the first imaging unit 21A and the observation depth $F_2$ of the second imaging unit 21B.

Figure 5:
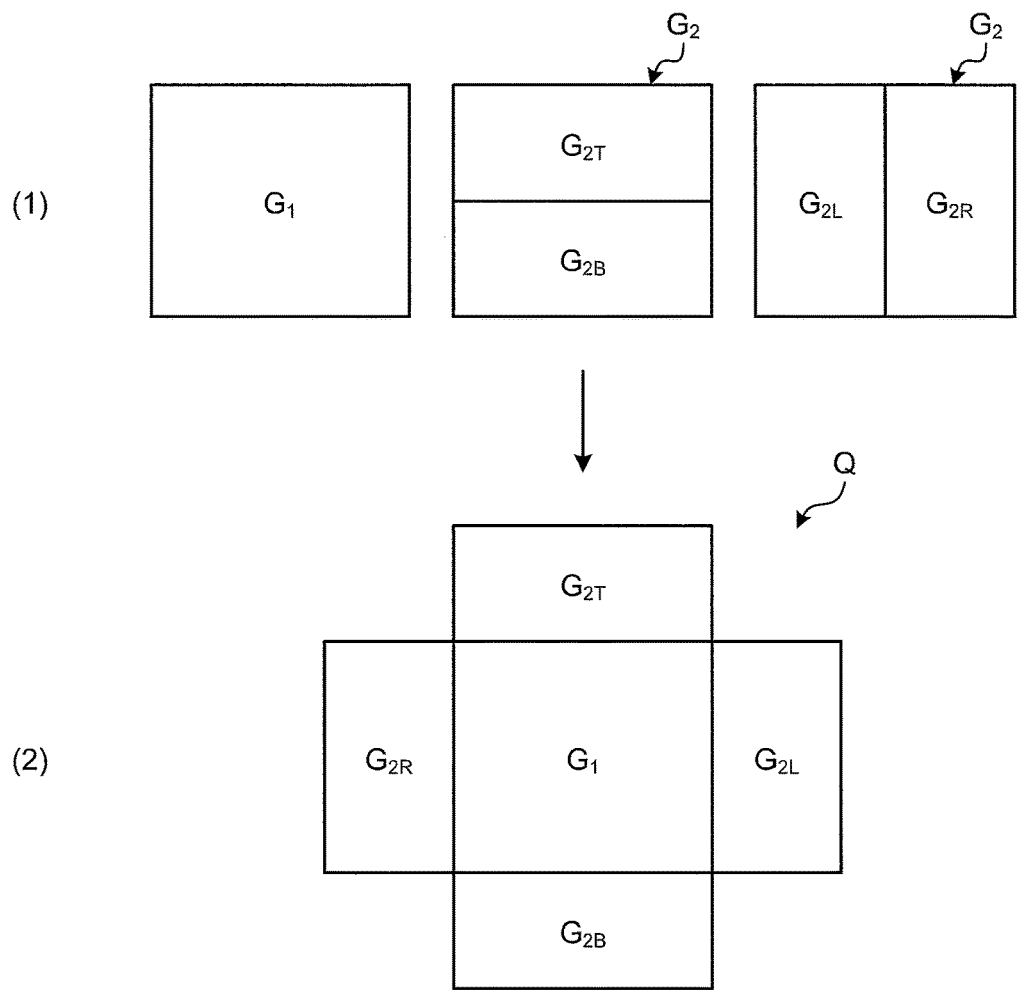
FIG. 5 is a diagram illustrating an image composition process performed by a display image generation unit illustrated in FIG. 2.

The display image generation unit 434 performs OSD processing or the like to generate, as a display image, a composite image in which the first image and the second image associated with each other by the association unit 433 are combined. The display image generation unit 434 divides the second image, and generates a composite image in which the divided image are arranged at peripheral edges of the first image. FIG. 5 is a diagram illustrating an image composition process performed by a display image generation unit 434. For example as illustrated in (1) of FIG. 5, the display image generation unit 434 vertically divides the second image $G_2$ to generate images $G_{2T}$ and $G_{2B}$, and horizontally divides the second image $G_2$ to generate images $G_{2L}$, and $G_{2R}$. As illustrated in (2) of FIG. 5, the display image generation unit 434 generates a composite image Q in which the image $G_{2T}$ is disposed above a first image $G_1$, the image $G_{2B}$ is disposed below the first image $G_1$, the image $G_{2L}$ is disposed on the right side of the first image $G_1$, and the image $G_{2R}$ is disposed on the left side of the first image $G_1$. Furthermore, the display image generation unit 434 may superimpose information about an in-vivo image, on the composite image Q. Here, the information includes information representing for example patient information, an examination content, or a main imaging unit of the first imaging unit 21A or the second imaging unit 21B.

The control unit 44 controls the component units of the receiving device 4. The control unit 44 includes a processor such as a CPU. The control unit 44 has a display control unit 441. The display control unit 441 performs predetermined processing such as data decimation according to an image display range of the display unit 46, or gradation processing, on a display image generated by the display image generation unit 434 of the image processing unit 43, and then outputs the display image to be displayed on the display unit 46.

The operating unit 45 is an input device used by the user to input various setting information or instruction information to the receiving device 4. The operating unit 45 includes for example a switch, a button, or the like provided at an operation panel of the receiving device 4. The operating unit 45 may include a switching button switching between the first imaging unit 21A and the second imaging unit 21B to select an imaging unit capturing an image as a main image of images to be displayed on the display unit 46 described below.

The display unit 46 displays an in-vivo image or the like based on the image received from the capsule endoscope 2. The display unit 46 includes a liquid crystal display, an organic EL display, or the like. The display unit 46 displays the composite image for display, generated by the display image generation unit 434, according to the control of the display control unit 441. The display unit 46 includes a liquid crystal screen or the like provided on a main surface of the receiving device 4.

The memory 47 stores values of various parameters used by the association unit 433, and association information output by the association unit 433, and the like, in addition to programs causing the receiving device 4 to operate to perform various functions, the imaging signals subjected to processing by the received signal processing unit 42, the images generated by the image processing unit 43, and the related information. The memory 47 includes a RAM, a ROM, and the like. The memory 47 also stores the values of $F_1$, $F_2$, and C described above, according to the type of the capsule endoscope 2.

The data transmission/reception unit 48 transmits the imaging signals and the related information stored in the memory 47 to the processing device 5, when communicably connected to the processing device 5. The data transmission/reception unit 48 includes a communication I/F such as a LAN.

Such a receiving device 4 is mounted to the subject H and carried, while the capsule endoscope 2 performs imaging (e.g., after the capsule endoscope 2 is swallowed by the subject H, and before the capsule endoscope 2 is discharged through the digestive tract). At the same time, the receiving device 4 further adds the related information such as reception strength information or reception time information at the receiving antennas 3a to 3h, to the imaging signals received through the receiving antenna unit 3, and causes the memory 47 to store these imaging signals and related information. Furthermore, the receiving device 4 synchronously displays the first image and the second image associated with the first image, on the display unit 46.

After the imaging by the capsule endoscope 2, the receiving device 4 is removed from the subject H, and is set to the cradle 5a (see FIG. 1) connected to the processing device 5. Thus, the receiving device 4 is communicably connected to the processing device 5, and transfers (downloads) the imaging signals and the related information stored in the memory 47 to the processing device 5.

The processing device 5 includes for example a workstation including the display device 6 such as a liquid crystal display. The processing device 5 includes a data transmission/reception unit 51, an image processing unit 52, a control unit 53 generally controlling respective units, a display control unit 54, an input unit 55, and a storage unit 56.

The data transmission/reception unit 51 is an interface connectable to a communication circuit such as a USE, a wired LAN, or a wireless LAN, and includes a USB port and a LAN port. In the embodiment, the data transmission/reception unit 51 is connected to the receiving device 4 through the cradle 5a connected to the USB port, and transmits and receives data with the receiving device 4.

The image processing unit 52 includes hardware such as a CPU, and reads a predetermined program stored in the storage unit 56 described later to perform predetermined image processing for generating an in-vivo image corresponding to an imaging signal input from the data transmission/reception unit 51 or an imaging signal stored in the storage unit 56.

The control unit 53 includes hardware such as a CPU, reads various programs stored in the storage unit 56 to transfer instructions or data to the units constituting the processing device 5, on the basis of for example signals input through the input unit 55 or the imaging signals input from the data transmission/reception unit 51, and generally controls the operation of the processing device 5 as a whole.

The display control unit 54 performs predetermined processing such as data decimation according to an image display range of the display device 6, or gradation processing, on an image generated by the image processing unit 52, and then outputs the image to be displayed on the display device 6.

The input unit 55 includes an input device such as a keyboard, a mouse, a touch panel, or various switches. The input unit 55 receives input of information or a command according to the operation by the user.

The storage unit 56 includes a semiconductor memory such as a flash memory, a RAM, or a ROM, a recording medium such as an HDD, an MO, a CD-R, or a DVD-R and a drive device driving the recording medium, or the like. The storage unit 56 stores programs causing the processing device 5 to operate to perform various functions, various information used during execution of the programs, the imaging signals and the related information acquired through the receiving device 4, and the like.

Figure 6:
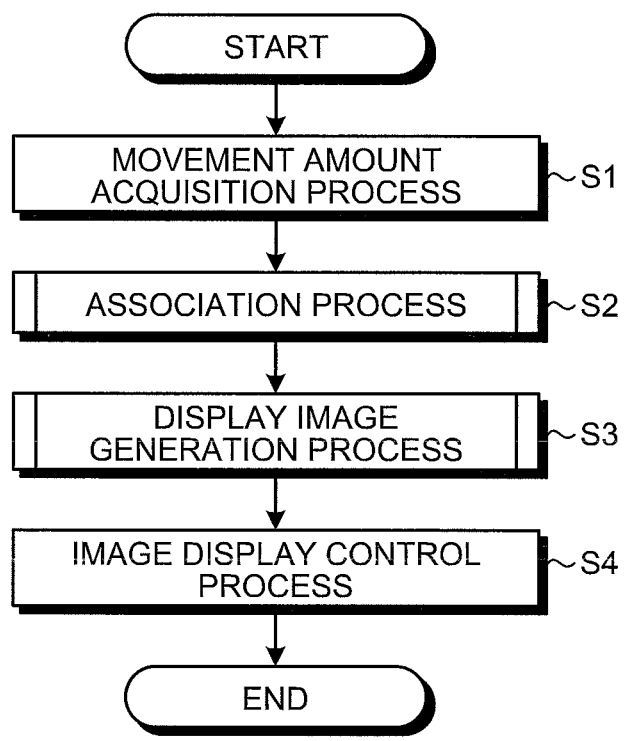
FIG. 6 is a flowchart illustrating a procedure of an image display process performed by a receiving device illustrated in FIG. 2.

Next, an image display process performed by the receiving device 4 will be described. FIG. 6 is a flowchart illustrating an exemplary procedure of the image display process performed by the receiving device 4.

As illustrated in FIG. 6, in the receiving device 4, a movement amount acquisition process is performed (step S1) in which the movement amount acquisition unit 432 acquires the movement amount of the capsule endoscope 2 in the movement direction, on the basis of the detection signal of the acceleration or the like detected by the motion sensor 28. The movement amount acquisition unit 432 acquires the movement amount of the capsule endoscope 2 in the movement direction, during a period from time at which the first imaging unit 21A captures the first image to be displayed, to time at which the first imaging unit 21A captures an image of a set subsequent to the first image.

The association unit 433 performs an association process associating the first image captured by the first imaging unit 21A, with the second image selected from images captured by the second imaging unit 21B, and captured with an effective imaging area continued from an effective imaging area of the first imaging unit 21A upon capturing the first image, on the basis of at least the imaging distance of the capsule endoscope 2 in the movement direction and the movement amount of the capsule endoscope 2 acquired by the movement amount acquisition unit 432 (step S2).

The display image generation unit 434 performs a display image generation process for generating, as the display image, a composite image in which the first image and the second image are associated with each other by the association unit 433 are combined (step S3).

The display control unit 441 performs the predetermined processing such as the data decimation according to the image display range of the display unit 46, or the gradation processing, on the display image generated in the display image generation processing, and then performs an image display control process for outputting the display image to be displayed on the display unit 46 (step S4).

Figure 7:
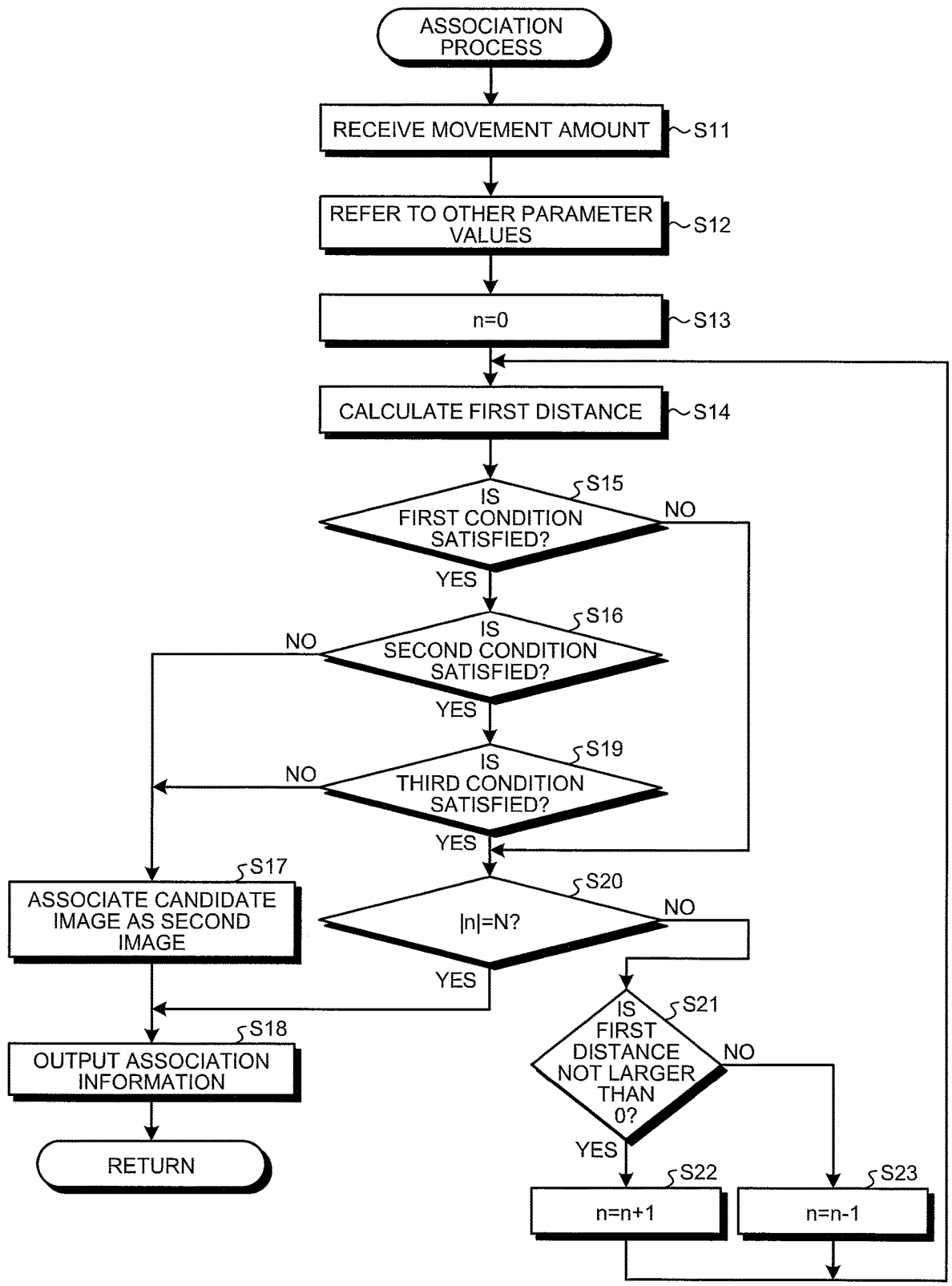
FIG. 7 is a flowchart illustrating a procedure of an association process illustrated in FIG. 6.
Figure 8:
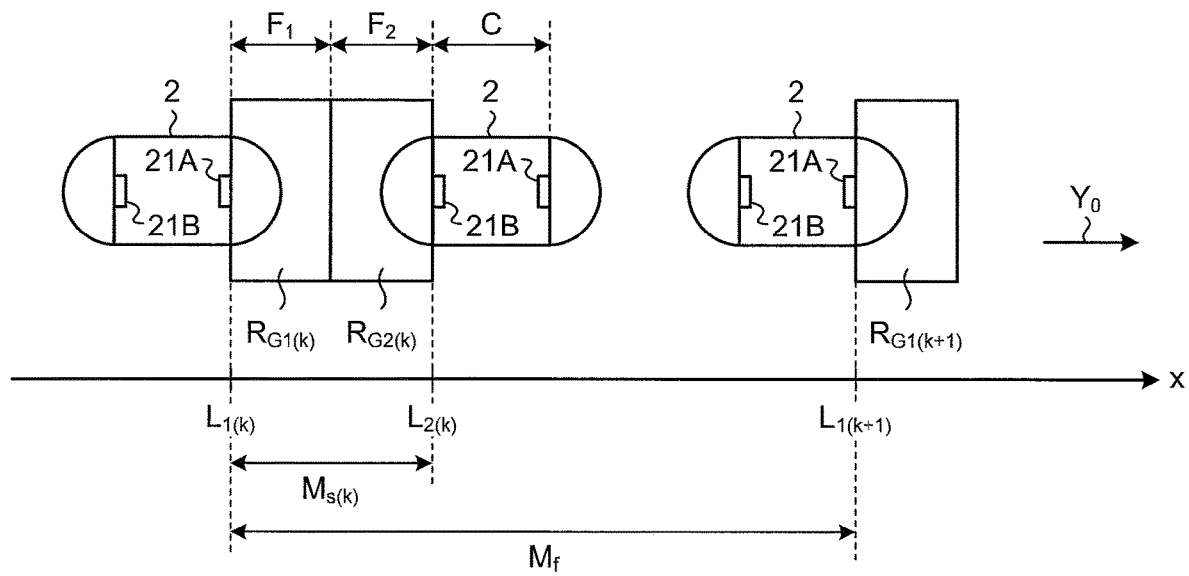
FIG. 8 is a diagram illustrating a movement state of the capsule endoscope illustrated in FIG. 2.

FIG. 7 is a flowchart illustrating an example of a procedure (step S2) of the association process illustrated in FIG. 6. For the purpose of description, the first image to be displayed, that is, the first image to be associated will be defined as an image $G_{1(k)}$ of the k-th set captured by the first imaging unit 21A. FIG. 8 is a diagram illustrating a movement state of the capsule endoscope illustrated in FIG. 2. In an example of FIG. 8, the capsule endoscope 2 moves as indicated by an arrow $Y_0$, where an x-axis and the imaging direction of the first imaging unit 21A are substantially coincide with each other. In the following description, an effective imaging area of the first imaging unit 21A upon capturing the first image $G_{1(k)}$ is represented by $R_{G1(k)}$, an effective imaging area of the first imaging unit 21A upon capturing an image $G_{1(k+1)}$ is represented by $R_{G1(k+1)}$, an image of the h-th set captured by the second imaging unit 21B is represented by $G_{2(1)}$, and an effective imaging area of the second imaging unit 21B upon capturing the image $G_{2(h)}$ is represented by $R_{G2(h)}$.

The association unit 433 receives, from the movement amount acquisition unit 432, a distance $M_f$ (see FIG. 8) as the movement amount of the capsule endoscope 2, during a period after the start of imaging the first image $G_{1(k)}$ by the first imaging unit 21A, and before the start of imaging the image $G_{1(k+1)}$ of the (k+1)th set subsequent to the first image $G_{1(k)}$ by the first imaging unit 21A (step S11).

The association unit 433 refers to the memory 47 for values of other parameters required for subsequent calculations (step S12). The parameters are the observation depths $F_1$ and $F_2$, and the distance C between the light receiving surface of the imaging element 21A-1 and the light receiving surface of the imaging element 21B-1.

In order to determine a second image to be associated with the first image $G_{1(k)}$, the association unit 433 sequentially determines whether a candidate image being a candidate for the second image satisfies predetermined conditions, from images captured by the second imaging unit 21B. The candidate image is an image $G_{2(h)}$ of the h-th set captured by the second imaging unit 21B. Furthermore, a difference (h−k) between a set number h of the set to which the candidate images $G_{2(h)}$ belongs, and a set number k of the set to which the first image $G_{1(k)}$ belongs is represented by n. The association unit 433 sets n to 0 (step S13). In other words, the association unit 433 sets the candidate image to an image $G_{2(k)}$ of the k-th set, identical to the set to which the first image $G_{1(k)}$ belongs, captured by the second imaging unit 21B.

The association unit 433 calculates the first distance, on the basis of the movement amount of the capsule endoscope 2 in the movement direction received in step S11 (step S14). Specifically, the first distance $M_{s(h)}$ is a distance between an x-coordinate ($L_{1(k)}$) of the position of the first imaging unit 21A upon starting to image the first image $G_{1(k)}$, and an x-coordinate ($L_{2(h)}$) of the position of the second imaging unit 21B upon starting to image the candidate image $G_{2(h)}$. That is, the first distance $M_{s(h)}$ can be calculated by formula (1A).

$$M_{s(h)} = L_{2(h)} - L_{1(k)} \tag{1A}$$

In FIG. 8, the candidate image is $G_{2(k)}$, and the first distance $M_{s(k)}$ can be calculated by formula (1B).

$$M_{s(k)} = L_{2(k)} - L_{1(k)} = M_f/2 - C \tag{1B}$$

Furthermore, when the capsule endoscope 2 moves at a constant speed, the first distance $M_{s(h)}$ is determined by formula (1C) on the basis of formula (1B).

$$M_{s(h)} = M_{s(k)} + M_f \times n \tag{1C}$$

The association unit 433 determines whether the image $G_{2(h)}$ satisfies a first condition that the first distance $M_{s(h)}$ is larger than 0 and is not larger than the imaging distance of the two imaging units (step S15). The first condition is defined as in formula (2A), using the first distance $M_{s(h)}$, $F_1$, and $F_2$.

$$0 < M_{s(h)} \le F_1 + F_2 \tag{2A}$$

The following formula (2B) is derived from formula (2A) on the basis of formula (1C).

$$0 < M_{s(k)} + M_f \times n + F_2 \tag{2B}$$

When the candidate image is the image $G_{2(k)}$ belonging to the same set as the first image $G_{1(k)}$, n=0 is set, and formula (2C) is derived from formula (2B).

$$0 < M_{s(k)} \le F_1 + F_2 \tag{2C}$$

Figure 9:
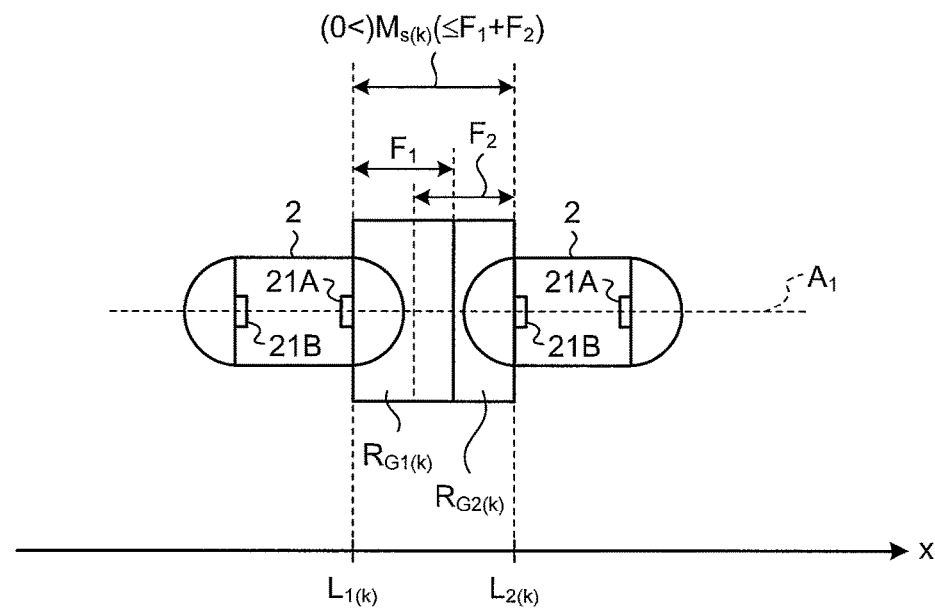
FIG. 9 is a diagram illustrating a first condition determined by an association unit illustrated in FIG. 2.
Figure 10:
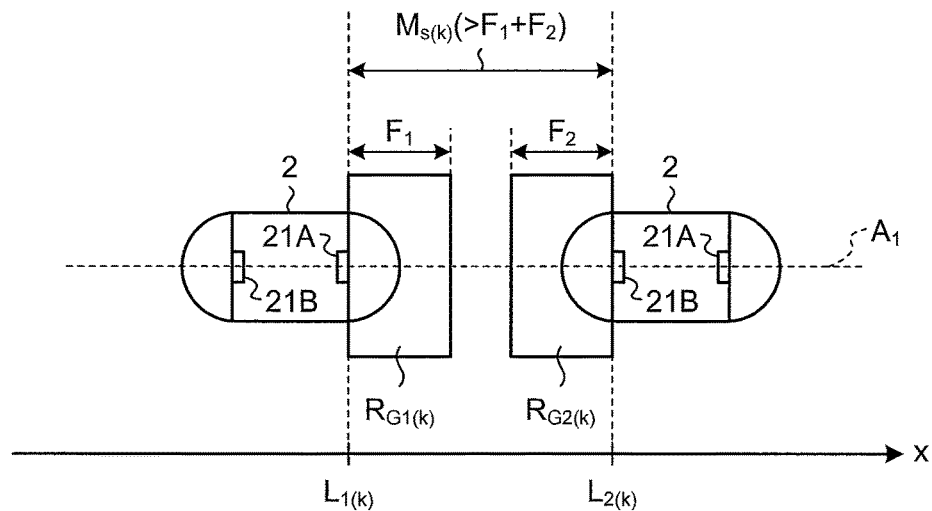
FIG. 10 is a diagram illustrating the first condition determined by the association unit illustrated in FIG. 2.

FIGS. 9 and 10 are diagrams illustrating the first condition. In FIGS. 9 and 10, when the candidate image is the image $G_{2(k)}$ of the k-th set identical to the set to which the first image $G_{1(k)}$ belongs, the first distance is $M_{s(k)}$. As illustrated in FIG. 9, when the first distance $M_{s(k)}$ satisfies formula (2C) as the first condition, the effective imaging area $R_{G1(k)}$ of the first imaging unit 21A upon capturing the first image $G_{1(k)}$, and an effective imaging area $R_{G2(k)}$ of the second imaging unit 21B upon capturing the image $G_{2(k)}$ overlap each other, thus the effective imaging area $R_{G2(k)}$ of the second imaging unit 21B upon capturing the image $G_{2(k)}$, and the effective imaging area $R_{G1(k)}$ of the first imaging unit 21A upon capturing the first image $G_{1(k)}$ have spatial continuity between the effective imaging area $R_{G2(k)}$ and the effective imaging area $R_{G1(k)}$. In contrast, as illustrated in FIG. 10, when the first distance $M_{s(k)}$ is larger than the sum of the observation depth $F_1$ and the observation depth $F_2$, and does not satisfy the first condition, there is no gap suitable for observation, between the effective imaging area $R_{G1(k)}$ of the first imaging unit 21A upon capturing the first image $G_{1(k)}$, and the effective imaging area $R_{G2(k)}$ of the second imaging unit 21B upon capturing the image $G_{2(k)}$. Therefore, the effective imaging area $R_{G2(k)}$ of the second imaging unit 21B upon capturing the image $G_{2(k)}$, and the effective imaging area $R_{G1(k)}$ of the first imaging unit 21A upon capturing the first image $G_{1(k)}$ have no spatial continuity between the effective imaging area $R_{G2(k)}$ and the effective imaging area $R_{G1(k)}$. Furthermore, similarly, when the first distance $M_{s(k)}$ is not larger than 0 and does not satisfy the first condition, there is no gap suitable for observation between the effective imaging area $R_{G1(k)}$ of the first imaging unit 21A upon capturing the first image $G_{1(k)}$, and the effective imaging area $R_{G2(k)}$ of the second imaging unit 21B upon capturing the image $G_{2(k)}$, and the effective imaging area $R_{G2(k)}$ of the second imaging unit 21B upon capturing the image $G_{2(k)}$, and the effective imaging area $R_{G1(k)}$ of the first imaging unit 21A upon capturing the first image $G_{1(k)}$ have no spatial continuity between the effective imaging area $R_{G2(k)}$ and the effective imaging area $R_{G1(k)}$.

When the first distance $M_{s(h)}$ is determined to satisfy the first condition (step S15: Yes), the association unit 433 determines whether the first distance $M_{s(h)}$ further satisfies a second condition defined using the first distance $M_{s(h)}$ and the observation depth $F_1$ (step S16). The second condition is defined using the following formula (3A).

$$0 \le M_{s(h)} \le F_1 \tag{3A}$$

The formula (3B) is derived from formula (3A) on the basis of formula (1C).

$$0 \le M_{s(k)} + M_f \times n \le F_1 \tag{3B}$$

Furthermore, when n=0 is set, formula (3C) is derived from formula (3B).

$$0 \le M_{s(k)} \le F_1 \tag{3C}$$

Satisfaction of formula (3C) by the first distance $M_{s(k)}$ represents that the second imaging unit 21B captures the image $G_{2(k)}$ in the observation depth $F_1$ of the first imaging unit 21A, and it cannot be denied that the effective imaging area $R_{G1(k)}$ of the first imaging unit 21A upon capturing the first image $G_{1(k)}$, and the effective imaging area $R_{G2(k)}$ of the second imaging unit 21B upon capturing the image $G_{2(k)}$ may completely overlap each other. In contrast, non-satisfaction of formula (3C) represents that the second imaging unit 21B captures the image $G_{2(k)}$ outside the observation depth $F_1$, and thus, although an effective imaging area continued from the effective imaging area $R_{G1(k)}$ of the first imaging unit 21A upon capturing the first image $G_{1(k)}$ is captured in the image. $G_{2(k)}$, the effective imaging area $R_{G1(k)}$ and the effective imaging area $R_{G2(k)}$ do not overlap each other, and the image $G_{2(k)}$ further includes an area outside the effective imaging area $R_{G1(k)}$ of the first imaging unit 21A upon capturing the first image $G_{1(k)}$.

When the first distance $M_{s(h)}$ is determined not to satisfy the second condition (step S16: No), the association unit 433 outputs association information (step S18) representing association of the candidate image to be determined, defined as the second image, with the first image (step S17), and the association process is finished.

When the first distance $M_{s(h)}$ is determined to satisfy the second condition (step S16: Yes), the association unit 433 determines whether the first distance $M_{s(h)}$ satisfies a third condition defined using the observation depth $F_1$ and the observation depth $F_2$ (step S19). The third condition is defined using the following formula (4A).

$$0 \leq M_{s(h)} + F_2 \leq F_1 \quad (4A)$$

The following formula (4B) is derived from formula (4A) on the basis of formula (10).

$$0 \leq M_{s(k)} + M_f \times n + F_2 \leq F_1 \quad (4B)$$

When n=0 is set, formula (4C) is derived from formula (4B).

$$0 \leq M_{s(k)} + F_2 \leq F_1 \quad (4C)$$

In an example of the first image $G_{1(k)}$ and the image $G_{2(k)}$ of the same set, satisfaction of formula (4C) by the sum of the first distance $M_{s(k)}$ corresponding to the first image $G_{1(k)}$ and the image $G_{2(k)}$, and the observation depth $F_2$ represents that the effective imaging area $R_{G2(k)}$ of the second imaging unit 21B upon capturing the image $G_{2(k)}$ is included in the effective imaging area $R_{G1(k)}$, as the observation depth $F_1$, of the first imaging unit 21A upon capturing the first image $G_{1(k)}$. In other words, the image $G_{2(k)}$ does not image an area different from the effective imaging area $R_{G1(k)}$, and the image $G_{2(k)}$ does not need to be displayed in synchronization with the first image $G_{1(k)}$.

When the third condition is determined not to be satisfied (step S19: No), the association unit 433 outputs the association information (step S18) representing association of the candidate image to be determined, defined as the second image, with the first image (step S17), and the association process is finished.

When the third condition is determined to be satisfied (step S19: Yes), or when the first condition is determined not to be satisfied (step S15: No), the association unit 433 determines whether an absolute value |n| of n is a maximum value N (step S20). For example, when the maximum value N is 2, the association unit 433 determines association of an image of a set two sets prior to or subsequent to the first image, captured by the second imaging unit 21B. Note that the maximum value N can be set to an arbitrary value by the user's operation or the like of the operating unit 45. When the absolute value |n| of n is determined to be the maximum value N (step S20: Yes), the association unit 433 outputs association information (step S18) representing association of no image with the first image, and the association process is finished.

In contrast, when the absolute value |n| of n is not the maximum value N (step S20: No), the association unit 433 then determines whether the first distance $M_{s(h)}$ calculated under the first condition is not larger than 0, in order to select a next candidate image which is determined whether to be associated (step S21).

When the first distance $M_{s(h)}$ is determined to be not larger than 0 (step S21: Yes), the association unit 433 performs processing for setting n=n+1 to increase the first distance $M_{s(h)}$ (step S22). That is, the association unit 433 defines an image $G_{2(h+1)}$ of a set subsequent to the image $G_{2(h)}$, captured by the second imaging unit 21B, as the candidate image, and the process returns to step S14.

When the first distance $M_{s(h)}$ is determined to be larger than 0 (step S21: No), the association unit 433 performs processing for setting n=n−1 to reduce the first distance $M_{s(h)}$ (step S23). That is, the association unit 433 defines an image $G_{2(h-1)}$ of a set prior to the image $G_{2(h)}$, captured by the second imaging unit 21B, as the candidate image, and the process returns to step S14. This processing is repeated to adjust the first distance to satisfy the first condition.

FIGS. 11 to 14 are specific diagrams illustrating the association process illustrated in FIG. 7. In FIGS. 11 to 14, the observation depths $F_1$ and $F_2$ are 20 mm, the distance C between the light receiving surface of the imaging element 21A-1 and the light receiving surface of the imaging element 21B-1 is 20 mm. Furthermore, the first imaging unit 21A and the second imaging unit 21B have an angle of view of 180°.

Figure 11:
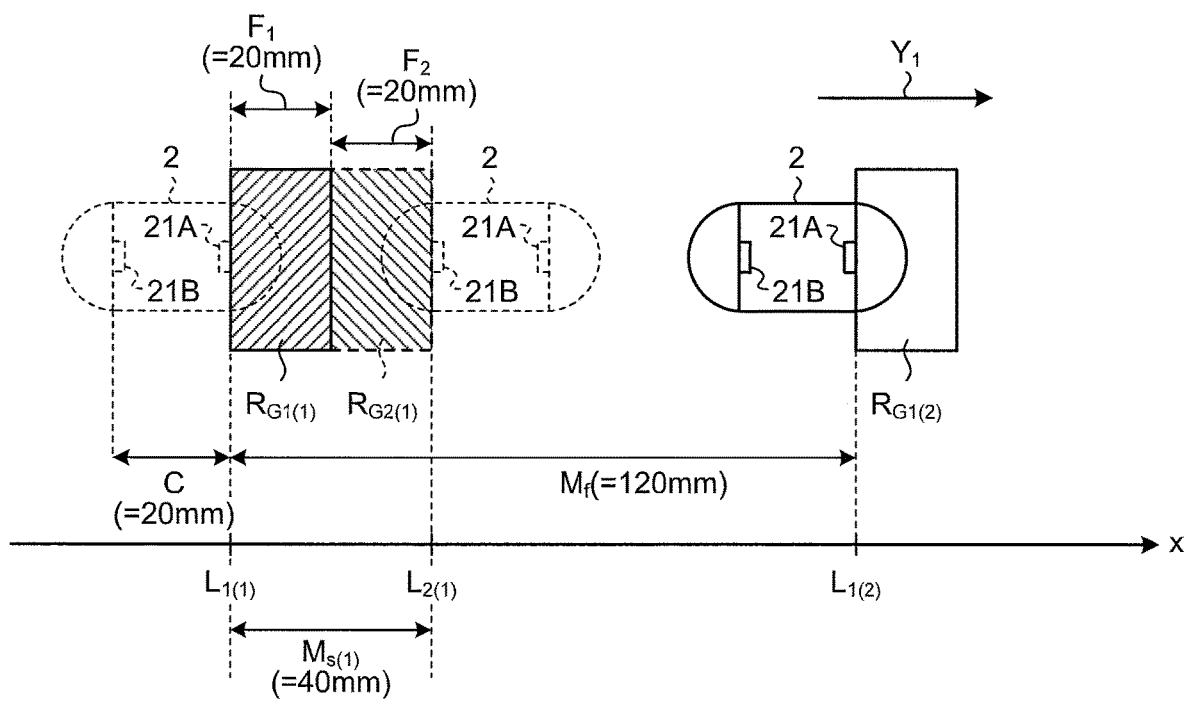
FIG. 11 is a specific diagram illustrating the association process illustrated in FIG. 7.

In FIG. 11, the image $G_{1(1)}$ captured at a position $L_{1(1)}$ by the first imaging unit 21A is the first image. In this configuration, as indicated by an arrow $Y_1$, the capsule endoscope 2 moves in the positive direction of the x-axis. The association unit 433 sets the value of n to 0 and defines, as the candidate image, the image $G_{2(1)}$ of a set identical to the set to which the first image $G_{1(1)}$ belongs, captured by the second imaging unit 21B, and determines the first condition. In this configuration, the distance $M_f$ is 120 mm, and the distance $M_f$ extends between an x-coordinate $(L_{1(1)})$ of a position of the first imaging unit 21A upon capturing the first image $G_{1(1)}$, and an x-coordinate $(L_{1(2)})$ of a position of the first imaging unit 21A upon capturing the image $G_{1(2)}$. A first distance $M_{s(1)}$ determined by formula (1B) is 40 mm, and has a value equal to 40 mm which is the sum of the observation depths $F_1$ and $F_2$ of, and thus, the first condition defined by formula (2C) is satisfied.

The association unit 433 determines the second condition for the image $G_{2(1)}$. In this configuration, the first distance $M_{s(1)}$ has a value of 20 mm, not larger than the observation depth $F_1$, and the second condition defined by formula (3C) is satisfied. Then, the association unit 433 determines the third condition. In the image $G_{2(1)}$, a value of $(M_{s(1)}+F_2)$ is 60 mm, and is larger than the observation depth $F_1$, and the third condition defined by formula (4C) is not satisfied. Accordingly, in an example of FIG. 11, the association unit 433 associates the image $G_{2(1)}$ being the candidate image and defined as the second image, with the first image $G_{1(1)}$.

Figure 12:
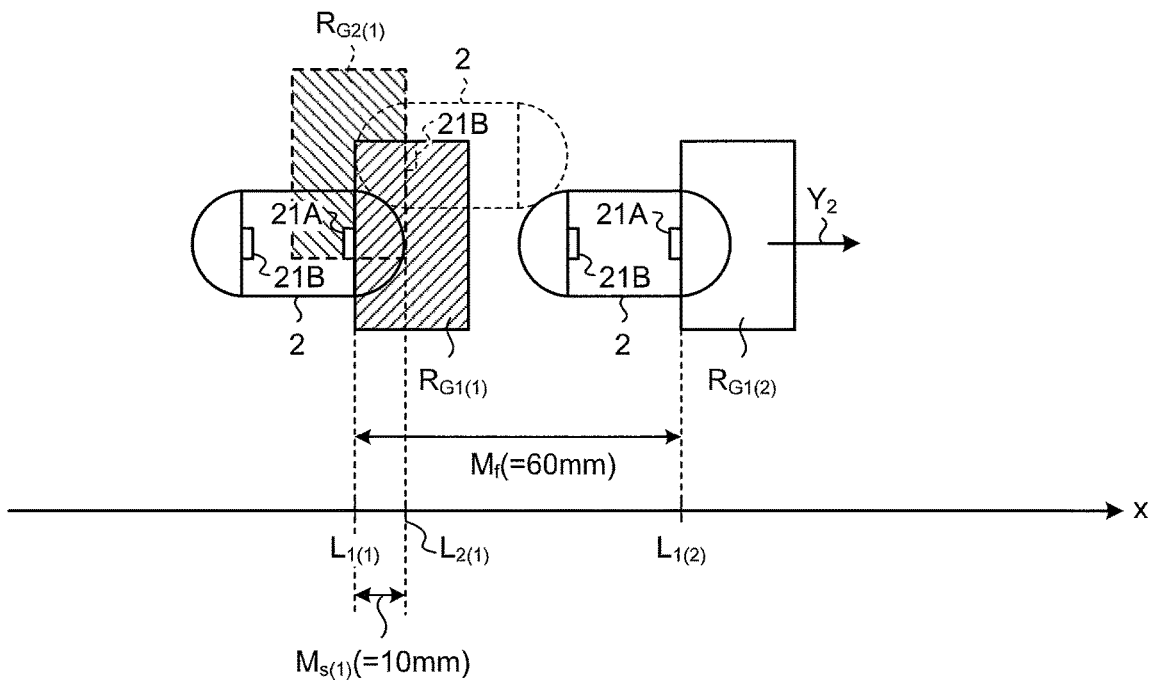
FIG. 12 is a specific diagram illustrating the association process illustrated in FIG. 7.

In FIG. 12, the distance $M_f$ is 60 mm. In this configuration, as indicated by an arrow $Y_2$, the capsule endoscope 2 moves in the positive direction of the x-axis. In an example of FIG. 12, the first distance $M_{s(1)}$ determined by formula (1B) is 10 mm, not larger than 40 mm which is the sum of the observation depths $F_1$ and $F_2$, and first condition defined by formula (2C) is satisfied. The association unit 433 determines the second condition for the image $G_{2(1)}$. In this configuration, the first distance $M_{s(1)}$ has a value not larger than the observation depth $F_1$, and the second condition defined by formula (3C) is satisfied. Then, the association unit 433 determines the third condition. In the image $G_{2(1)}$, a value of $(M_{s(1)}+F_2)$ is 30 mm, and is larger than the observation depth $F_1$, and the third condition defined by formula (4C) is not satisfied. Accordingly, in an example of FIG. 12, too, the association unit 433 associates the image $G_{2(1)}$ being the candidate image and defined as the second image, with the first image $G_{1(1)}$. Note that, in FIG. 12, the positions of the capsule endoscope 2 are illustrated to be vertically displaced, for convenience of description.

Figure 13:
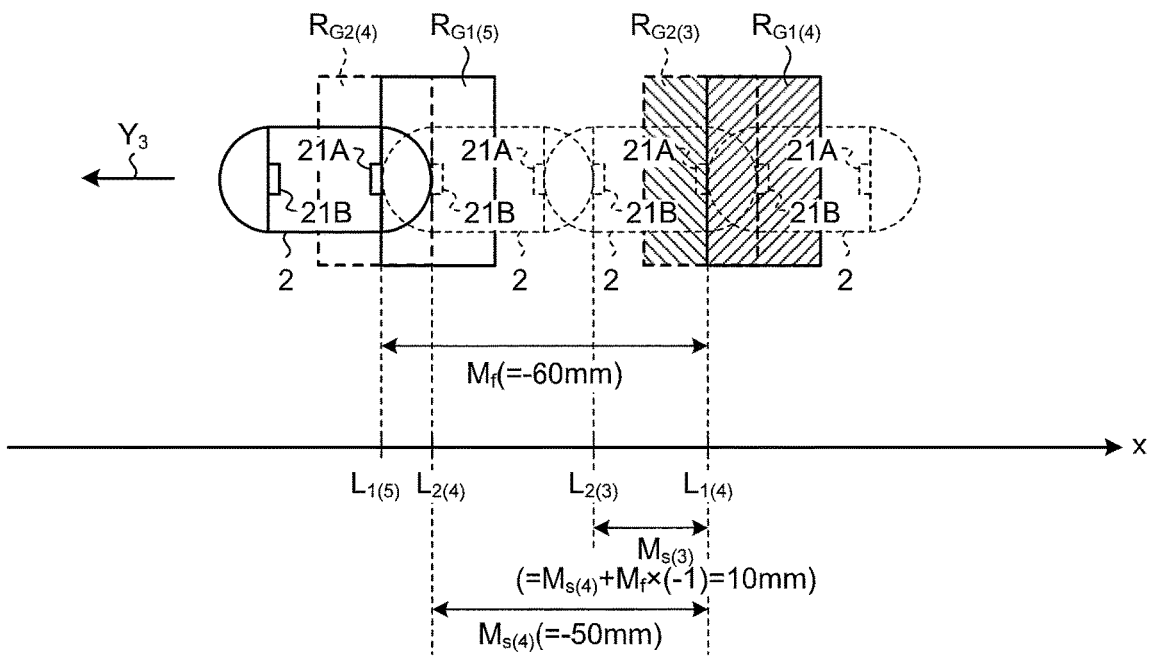
FIG. 13 is a specific diagram illustrating the association process illustrated in FIG. 7.

In FIG. 13, the first image $G_{1(4)}$ captured at a position $L_{1(4)}$ by the first imaging unit 21A is an object to be associated. In this configuration, as indicated by an arrow $Y_3$, the capsule endoscope 2 moves in the negative direction of the x-axis. First of all, the association unit 433 defines, as the candidate image, an image $G_{2(4)}$ of the fourth set identical to the set to which the first image $G_{1(4)}$ belongs, captured by the second imaging unit 21B, and determines the first condition. The distance $M_f$ is (−60) mm, and the distance $M_f$ extends between an x-coordinate $(L_{1(4)})$ of a position of the first imaging unit 21A upon capturing the first image $G_{1(4)}$, and an x-coordinate $(L_{1(5)})$ of a position of the first imaging unit 21A upon capturing the image $G_{1(5)}$. In this configuration, a first distance $M_{s(4)}$ determined by formula (1B) is (−50) mm, not larger than 0, and the first condition defined by formula (2B) is not satisfied.

In formula (2C), a value of the first distance $M_{s(4)}$ is not larger than 0, so that the association unit 433 sets n=−1, and defines, as the candidate image, the image $G_{2(3)}$ captured in a set one set prior to the first image $G_{1(4)}$. In this configuration, a value of $(M_{s(4)}+M_f\times n)$ being a first distance $M_{s(3)}$, which is determined by formula (1C), is $(-50+(-60)\times(-1))$ =10 mm, and the first condition defined by formula (2B) is satisfied.

The association unit 433 determines the second condition for the image $G_{2(3)}$. In this configuration, as described above, a value of $(M_{s(4)}+M_f\times n)$ is 10 mm, and is not larger than the observation depth $F_1$, and the second condition defined by formula (3B) is satisfied. Thus, the association unit 433 determines the third condition. In this configuration, a value of $(M_{s(4)}+M_f\times n+F_2)$ is 30 mm, and is larger than the observation depth $F_1$, and the third condition defined by formula (4B) is not satisfied. Accordingly, in an example of FIG. 13, the association unit 433 associates the first image $G_{1(4)}$ with the image $G_{2(3)}$.

Figure 14:
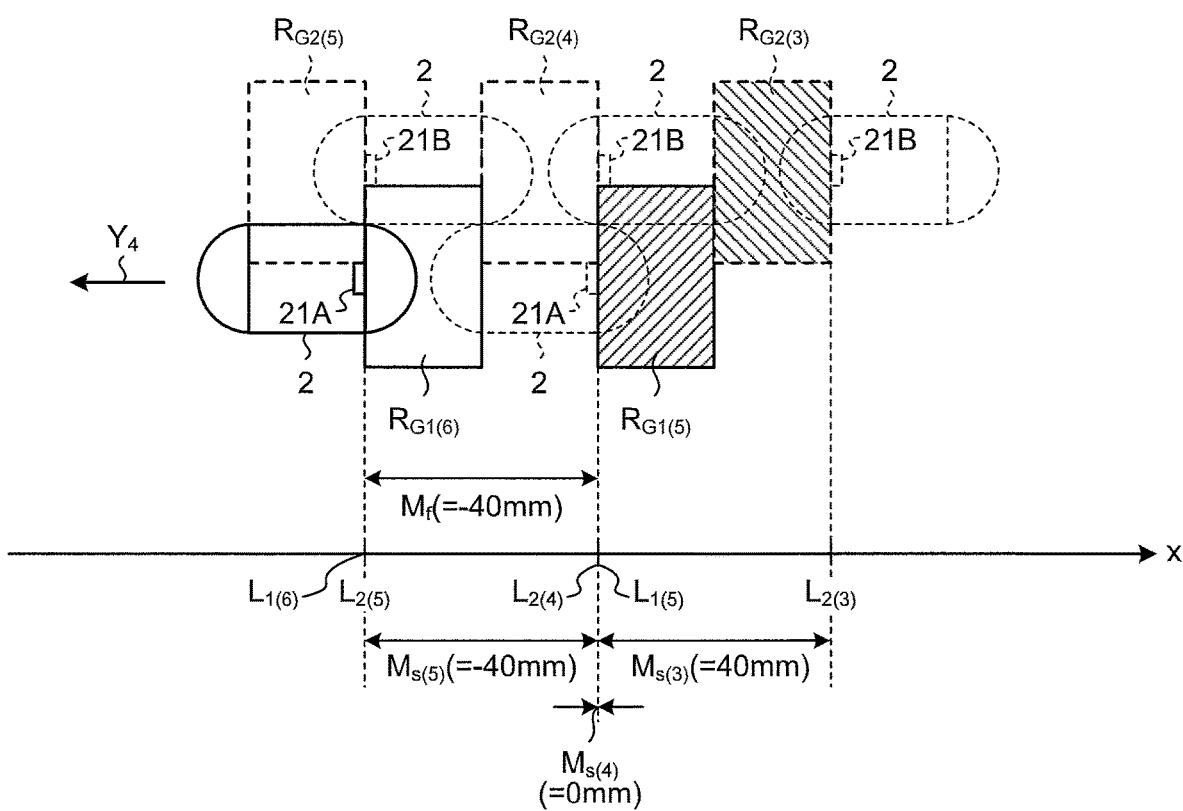
FIG. 14 is a specific diagram illustrating the association process illustrated in FIG. 7.

In FIG. 14, the image $G_{1(5)}$ captured at a position $L_{1(5)}$ by the first imaging unit 21A is the first image. In this configuration, as indicated by an arrow $Y_4$, the capsule endoscope 2 moves in the negative direction of the x-axis. First of all, the association unit 433 defines, as the candidate image, an image $G_{2(5)}$ of a set identical to the set to which the first image $G_{1(5)}$ belongs, captured by the second imaging unit 21B, and determines the first condition. The distance $M_f$ in the movement direction is (−40) mm, and the distance $M_f$ extends between an x-coordinate $(L_{1(5)})$ of a position of the first imaging unit 21A upon capturing the first image $G_{1(5)}$, and an x-coordinate $(L_{1(6)})$ of a position of the first imaging unit 21A upon capturing the image $G_{1(6)}$. In this configuration, a first distance $M_{s(5)}$ determined by formula (1B) is (−40) mm, not larger than 0, and the first condition defined by formula (2C) is not satisfied.

In formula (2C), a value of the first distance $M_{s(5)}$ is not larger than 0, so that the association unit 433 sets n=−1, and defines, as the candidate image, the image $G_{2(4)}$ captured in the fourth set one set prior to the first image $G_{1(5)}$. In this configuration, a value of $(M_{s(5)}+M_f\times n)$ being the first distance $M_{s(4)}$ is $(-40+(-40)\times(-1))$=0 mm, and the first condition defined by formula (2B) is not satisfied.

In formula (2B), a value of $(M_{s(5)}+M_f\times n)$ is not larger than 0, so that the association unit 433 sets n=−2, and defines, as the candidate image, the image $G_{2(3)}$ captured in the third set two sets prior to the first image $G_{1(5)}$. In this configuration, a value of $(M_{s(5)}+M_f\times n)$ is $(-40+(-40)\times(-2))$=40 mm, and the first condition defined by formula (2B) is satisfied. The association unit 433 determines the second condition for the image $G_{2(3)}$. In this configuration, as described above, the value of $(M_{s(5)}\ M_f\times n)$ is 40 mm and is larger than the observation depth $F_1$, and the second condition defined by formula (3B) is not satisfied. Accordingly, in an example of FIG. 14, the association unit 433 associates the first image $G_{1(5)}$ with the image $G_{2(3)}$. Note that, in FIG. 14, the positions of the capsule endoscope 2 are illustrated to be vertically displaced, for convenience of description.

Figure 15:
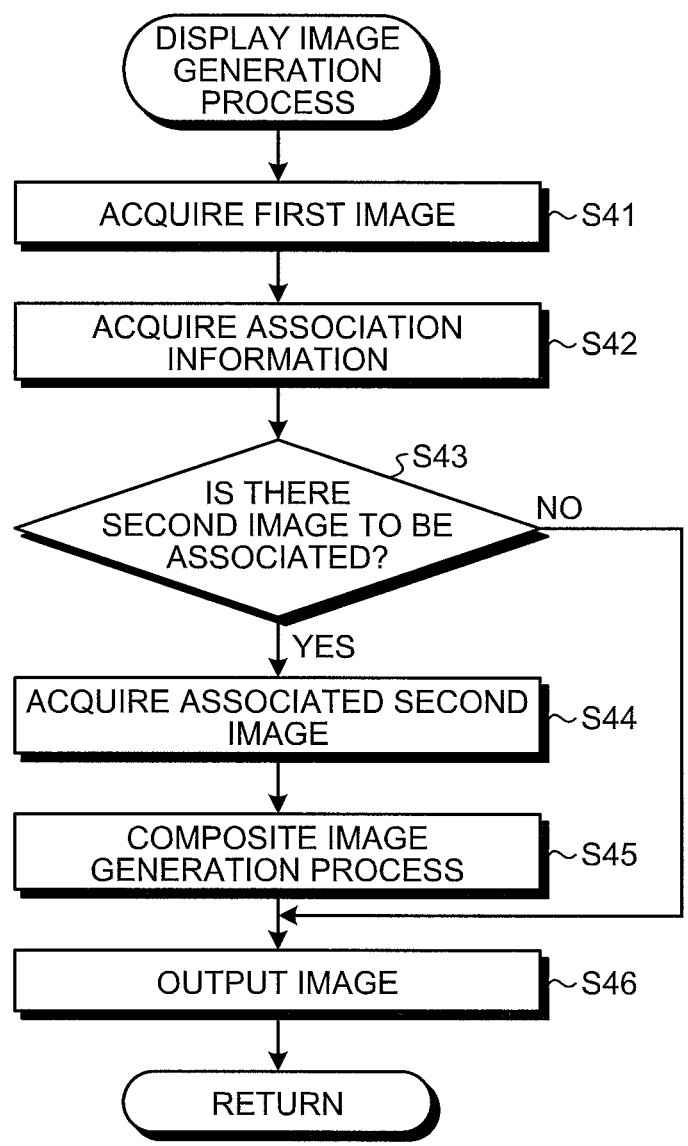
FIG. 15 is a flowchart illustrating a procedure of a display image generation process illustrated in FIG. 6.

Next, the display image generation process (step S3) illustrated in FIG. 6 will be described. FIG. 15 is a flowchart illustrating a procedure of the display image generation process illustrated in FIG. 6. The display image generation unit 434 acquires the first image to be displayed from images generated by the image generation unit 431 (step S41). The display image generation unit 434 acquires association information for the first image to be displayed, from the association unit 433 (step S42). The display image generation unit 434 determines whether there is a second image to be associated with the first image to be displayed, on the basis of the acquired association information (step S43). When it is determined that there is a second image to be associated with the first image to be displayed (step S43: Yes), the display image generation unit 434 acquires the second image associated with the first image from images generated by the image generation unit 431 (step S44). Composite image generation process is performed to generate a composite image in which the first image and the second image are combined (step S45), and the generated composite image is output as the display image to the control unit 44 (step S46).

Figure 16:
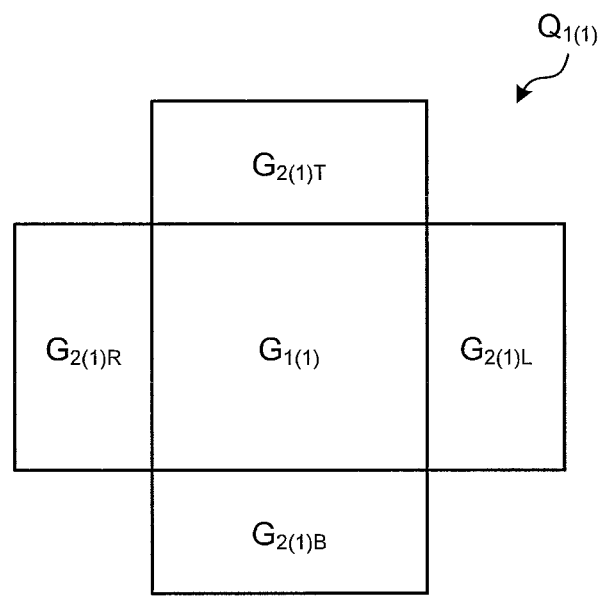
FIG. 16 is a diagram illustrating an example of a composite image generated by the display image generation unit illustrated in FIG. 2.

FIG. 16 is a diagram illustrating an example of the composite image generated by the display image generation unit 434. As exemplified in FIG. 5, when the association unit 433 associates the image $G_{2(1)}$ captured by the second imaging unit 21B, and defined as the second image, with the first image $G_{1(1)}$ to be displayed, the display image generation unit 434 vertically divides the image $G_{2(1)}$ as the second image to generate images $G_{2(1)T}$ and $G_{2(1)B}$, and horizontally divides the image $G_{2(1)}$ to generate images $G_{2(1)L}$ and $G_{2(1)R}$. The display image generation unit 434 generates a composite image $Q_{1(1)}$ in which the image $G_{2(1)T}$ is disposed above the first image $G_{1(1)}$, the image $G_{2(1)B}$ is disposed below the first image $G_{1(1)}$, the image $G_{2(1)L}$ is disposed on the right side of the first image $G_{1(1)}$, and the image $G_{2(1)R}$ is disposed on the left side of the first image $G_{1(1)}$. Note that whether to arrange the horizontally divided images $G_{2(1)L}$ and $G_{2(1)R}$ on the right or left side of the first image $G_{1(1)}$ is changed according to an actual movement direction of the capsule endoscope 2. FIG. 16 illustrates an example of the composite image where the capsule endoscope 2 moves along the positive direction of the x-axis, and when the capsule endoscope 2 is moved along the negative direction of the x-axis, the images $G_{2(1)L}$ and $G_{2(1)R}$ are arranged reversely of those of FIG. 16.

When it is determined that there is no second image to be associated with the first image to be displayed (step S43: No), the display image generation unit 434 outputs, as the display image, only the first image to be displayed to the control unit 44 (step S46).

As described above, in the embodiment, determination of the first to third conditions defined by simple formulas described above is only required to select a second image captured with an effective imaging area continued from an effective imaging area of the first imaging unit 21A upon capturing the first image, from a large number of images, and associate the second image with the first image. Thus, according to the embodiment, two images showing a spatially continuous area between the two images can be associated with each other by a simple process.

Figure 17:
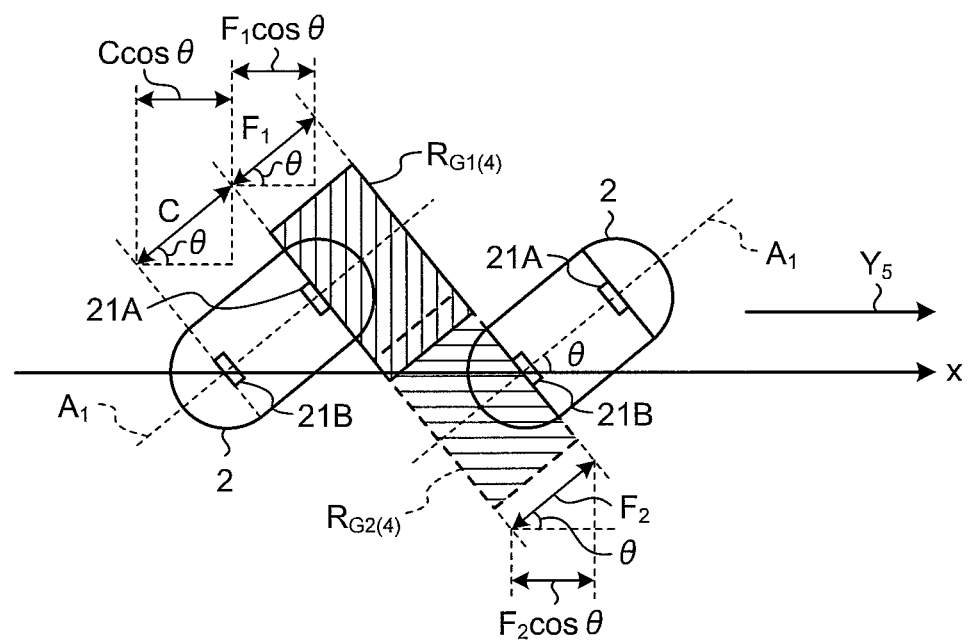
FIG. 17 is a diagram illustrating a first modification of the embodiment.

First modification of embodiment FIG. 17 is a diagram illustrating a first modification of the embodiment. As illustrated in FIG. 17, in the first modification of the embodiment, the optical axis $A_1$ of the capsule endoscope 2 and the x-axis crossing each other, that is, movement of the capsule endoscope 2 being inclined at a constant angle relative to a linear movement direction will be described. Note that, as indicated by an arrow $Y_5$, the capsule endoscope 2 moves in the positive direction of the x-axis. The association unit 433 acquires an angle θ between the optical axis $A_1$ of the capsule endoscope 2 and the x-axis corresponding to the movement direction of the capsule endoscope 2, on the basis of a detection result of the motion sensor 28 of the capsule endoscope 2. Then, the association unit 433 preferably uses for example the imaging distances of the first imaging unit 21A and the second imaging unit 21B on the x-axis, which are corrected according to the acquired angle θ, to perform the association process. That is, instead of formulas (1B) to (4B), formulas (1B-1) to (4B-1) obtained by correcting formulas (1B) to (4B) using the angle θ are used to determine the first to third conditions.

$$M_{s(k)} = (M_f/2) - C \cos\theta \quad (1B\text{-}1)$$

$$0 < M_{s(h)} \le F_1 \cos\theta + F_2 \cos\theta \quad (2A\text{-}1)$$

$$0 < M_{s(k)} + M_f \times n \le F_1 \cos\theta + F_2 \cos\theta \quad (2B\text{-}1)$$

$$0 < M_{s(h)} \le F_1 \cos\theta \quad (3A\text{-}1)$$

$$0 \le M_{s(k)} + M_f \times n \le F_1 \cos\theta \quad (3B\text{-}1)$$

$$0 \le M_{s(h)} + F_2 \cos\theta \le F_1 \cos\theta \quad (4A\text{-}1)$$

$$0 \le M_{s(k)} + M_f \times n + F_2 \cos\theta \le F_1 \cos\theta \quad (4B\text{-}1)$$

Note that the range of the angle θ to which formulas (1B-1) to (4B-1) are applied is preferably set appropriately according to calculation performance or the like of the association unit 433. For example, according to the calculation performance of the association unit 433, when the angle θ exceeds 10°, formulas (1B-1) to (4B-1) are applied, and when the angle θ is less than 10°, formulas (1B) to (4B) are used for convenience of calculation processing.

Figure 18:
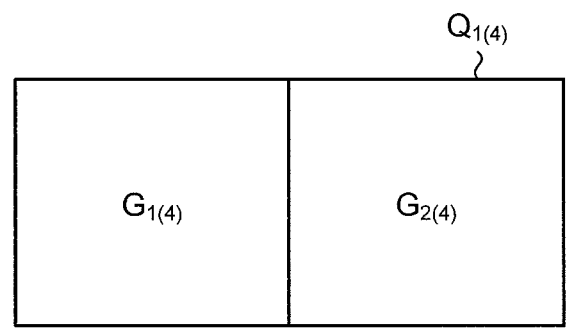
FIG. 18 is a diagram illustrating an example of the composite image generated by the display image generation unit illustrated in FIG. 2.

FIG. 18 is a diagram illustrating an example of the composite image generated by the display image generation unit 434. When the angle θ exceeds a predetermined threshold larger than 0°, for example, the angle θ is 45°, an image $Q_{1(4)}$ may be generated which is obtained by combining the first image $G_{1(4)}$ to be displayed and the second image $G_{2(4)}$ associated with the first image $G_{1(4)}$ in parallel.

Second Modification of Embodiment

In a second modification of the embodiment, a description will be made of the angle θ of 90° between the optical axis $A_1$ of the capsule endoscope 2 and the x-axis corresponding to the movement direction of the capsule endoscope 2.

Figure 19:
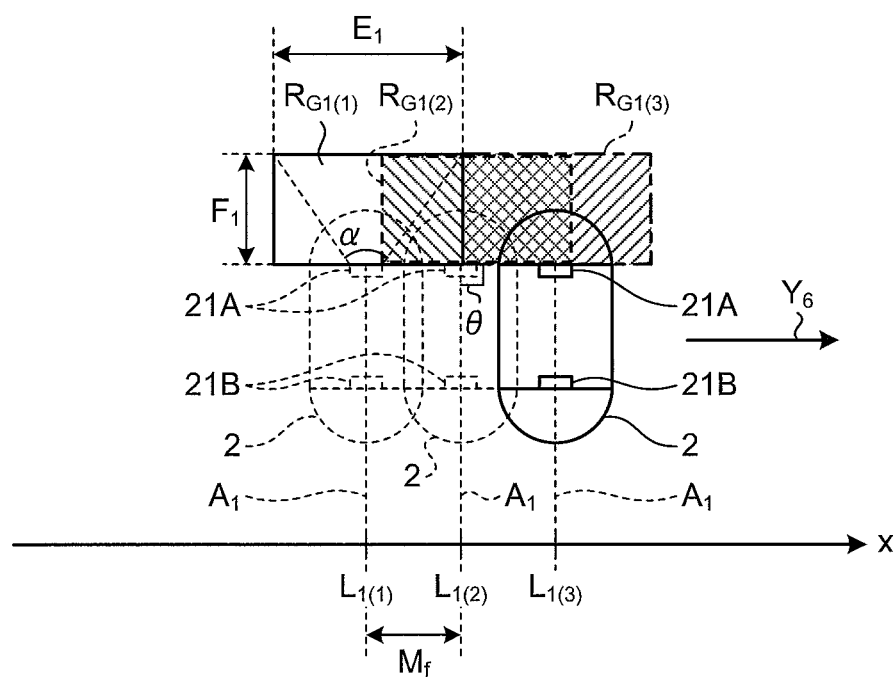
FIG. 19 is a diagram illustrating an example corresponding to a second modification of the embodiment.

FIG. 19 is a diagram illustrating an example corresponding to the second modification of the embodiment. Note that, as indicated by an arrow $Y_6$, the capsule endoscope 2 moves in the positive direction of the x-axis. As illustrated in FIG. 19, when the angle θ is 90°, the effective imaging area for an image captured by the first imaging unit 21A, and the effective imaging area for an image captured by the second imaging unit 21B have no continuity between the effective imaging area for an image captured by the first imaging unit 21A, and the effective imaging area for an image captured by the second imaging unit 21B, and the association unit 433 selects a second image from a group of images captured by the first imaging unit 21A. In this configuration, the association unit 433 determines the first condition defined by formula (2B-2), instead of formula (2B) used for the first condition. Note that the association unit 433 does not select the second image from a group of images captured by the second imaging unit 21B, so that the association unit 433 preferably associates an image satisfying the first condition defined by formula (2B-2) and defined as the second image, with the first image, without determination of the second condition and the third condition. Furthermore, $M_{s(h)}$ calculated in the embodiment is not used, and calculation thereof is not required.

$$0 < M_f + M_f \times (n-1) \quad (2B\text{-}2)$$

As illustrated in FIG. 19, $E_1$ in formula (2B-2) represents the imaging distance of the first imaging unit 21A on the x-axis upon movement of the capsule endoscope 2 while maintaining the optical axis $A_1$ perpendicular to the x-axis, and is a distance on a straight line having a distance equal to the observation depth $F_1$ along the optical axis $A_1$, from the light receiving surface of the first imaging unit 21A, of straight lines parallel with the light receiving surface within a field of view corresponding to an angle of view α of the first imaging unit 21A.

For example, in an example illustrated in FIG. 19, $E_1$ is 20 mm, and the distance $M_f$ is 10 mm. The association unit 433 determines, as the candidate image, the image $G_{1(2)}$ captured by the first imaging unit 21A, in the second set subsequent to the first image $G_{1(1)}$ of the first set. In this configuration, n is 1. A value of $(M_f + M_f \times (n-1))$ in formula (2B-2) is 10 mm, and less than $E_1$, so that the image $G_{1(2)}$ being the candidate image is associated as the second image with the first image $G_{1(1)}$, in the example of FIG. 19.

Figure 20:
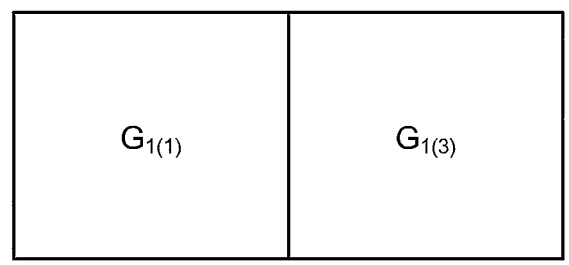
FIG. 20 is a diagram illustrating an example of the composite image generated by the display image generation unit illustrated in FIG. 2.

Note that, in the example of FIG. 19, the image $G_{1(3)}$ of a set subsequent to the set of the first image $G_{1(1)}$ by two sets may be further determined as the candidate image. In this configuration, n is 2, and the value of $(M_f + M_f \times (n-1))$ in formula (2B-2) is 20 mm and equal to $E_1$. Thus, the image $G_{1(3)}$ also satisfies the first condition, and the image $G_{1(3)}$ can be also associated as the second image with the first image $G_{1(1)}$. An overlapping area between an effective imaging area $R_{G1(1)}$ of the first imaging unit 21A upon capturing the first image $G_{1(1)}$, and an effective imaging area $R_{G1(3)}$ of the first imaging unit 21A upon capturing the image $G_{1(3)}$ is smaller than an overlapping area between the effective imaging area $R_{G1(1)}$ of the first imaging unit 21A upon capturing the first image $G_{1(1)}$, and an effective imaging area $R_{G1(2)}$ of the first imaging unit 21A upon capturing the image $G_{1(2)}$. In other words, information amount of the first image $G_{1(1)}$ and the image $G_{1(3)}$ is larger than information amount of the first image $G_{1(1)}$ and the image $G_{1(2)}$. Thus, the association unit 433 may associate the image $G_{1(3)}$ as the second image with the first image $G_{1(1)}$, where the image $G_{1(3)}$ satisfies formula (2B-2), and the value of $(M_f + M_f \times (n-1))$ in formula (2B-2) is closer to E1, In this configuration, the display image generation unit 434 may also generate a composite image in which the first image $G_{1(1)}$ and the image $G_{1(3)}$ are arranged in parallel, as indicated in FIG. 20, to be displayed on the display unit 46.

Figure 21:
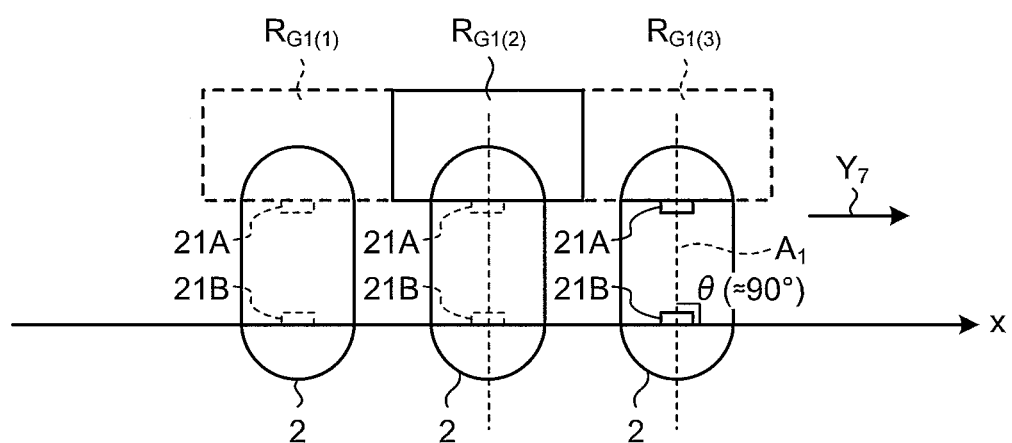
FIG. 21 is a diagram illustrating another example corresponding to the second modification of the embodiment.
Figure 22:
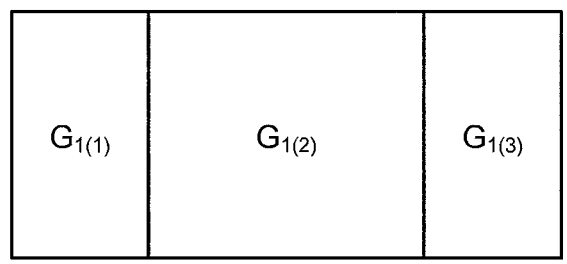
FIG. 22 is a diagram illustrating an example of the composite image generated by the display image generation unit illustrated in FIG. 2.

Furthermore, as in an example of FIG. 21 in which the capsule endoscope 2 moves in the positive direction of the x-axis, as indicated by an arrow $Y_7$, when both of the image $G_{1(1)}$ of a set prior to the first image $G_{1(2)}$, and the image $G_{1(3)}$ of a set subsequent to the first image $G_{1(2)}$ satisfy formula (2B-2), and the value of $(M_f+M_f\times(n-1))$ in formula (2B-2) has the same value in both of the image $G_{1(1)}$ and the image $G_{1(3)}$, either of the image $G_{1(1)}$ and the image $G_{1(3)}$ may be associated as the second image. In this configuration, the display image generation unit 434 may generate a composite image in which the first image $G_{1(2)}$, the image $G_{1(1)}$, and the image $G_{1(3)}$ are arranged in the imaging order, as illustrated in FIG. 22, to be displayed on the display unit 46.

Furthermore, a description is made of an example of the receiving device 4 displaying any of the images captured by the first imaging unit 21A as the first image, where the first imaging unit 21A is employed as the main imaging unit for image display, but as a matter of course, the second imaging unit 21B can be employed as the main imaging unit to perform the processing. The receiving device 4 may has a button switching the first image to be displayed, between an image captured by the first imaging unit 21A and an image captured by the second imaging unit 21B. Furthermore, in the present embodiment, for the purpose of description of the angle θ, the x-axis is used in which the optical axis $A_1$ of the capsule endoscope 2 and the movement direction of the capsule endoscope 2 coincide with each other, and the rightward direction corresponding to the imaging direction of the first imaging unit 21A of the capsule endoscope 2 is defined as the positive direction, but the leftward direction of the x-axis may be defined as the positive direction. Furthermore, in the receiving device 4, the main imaging unit in the image processing may be switched to the other, according to the movement direction of the capsule endoscope 2. For example, the receiving device 4 may perform processing with an imaging unit having the movement direction and the imaging direction substantially coinciding with each other, as the main imaging unit. When the movement amount calculated by the movement amount acquisition unit 432 has a negative value, the receiving device 4 switches the main imaging unit to a sub-imaging unit to perform processing, in order to respond to reversal in movement direction of the capsule endoscope 2.

Third Modification of Embodiment

The present embodiment can be also applied to a monocular capsule endoscope. That is, the capsule endoscope has a configuration from which the second imaging unit 21B and the second illumination unit 22B of the capsule endoscope 2 illustrated in FIG. 2 are eliminated.

In this configuration, the image generation unit 431 generates an image on the basis of the imaging signal from the first imaging unit 21A. As in step S1 of FIG. 6, the movement amount acquisition unit 432 acquires the movement amount of the capsule endoscope 2 in the movement direction, during a period from time at which the first imaging unit 21A captures the first image to be displayed, to time at which the first imaging unit 21A captures an image of a set subsequent to the first image. The association unit 433 acquires the angle θ between the optical axis $A_1$ of the capsule endoscope 2 and the x-axis corresponding to the movement direction of the capsule endoscope 2, on the basis of a detection result of the motion sensor 28 of the capsule endoscope 2. When the angle θ is 0°, the association unit 433 associates no image as the second image with the first image to be displayed.

When the angle θ is 90°, an image satisfying the first condition according to formula (2B-2) is preferably associated as the second image with the first image, as in the second modification of the embodiment. Note that, as in the second modification of the embodiment, the association unit 433 may define a plurality of images captured prior to and subsequent to the first image $G_{1(k)}$, as the candidate images, and associate an image of the candidate images, as the second image, with the first image $G_{1(k)}$, where the image as the second image satisfies formula (2B-2), and the value of $(M_f+M_f\times(n-1))$ in formula (2B-2) is closer to $E_1$. Furthermore, it is preferable that a predetermined range around 90° is appropriately set for the angle θ, and formula (2B-2) is applied to the angle θ.

Fourth Modification of Embodiment

Figure 23:
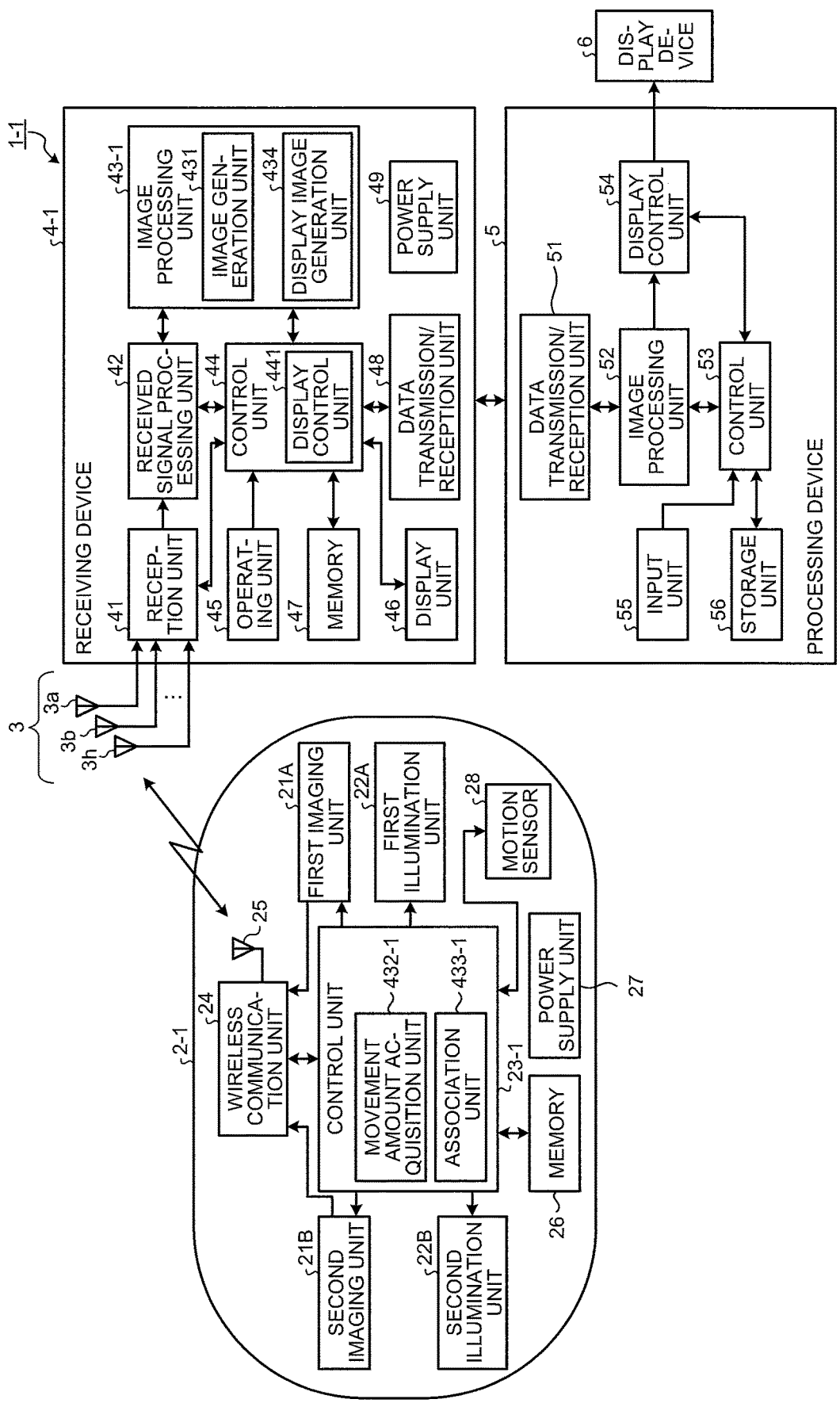
FIG. 23 is a block diagram illustrating a configuration of a capsule endoscope system according to a fourth modification of the embodiment.

In the embodiment and the first to third modifications of the embodiment, an example of the receiving device 4 having the image processing unit 43 and performing the association process has been described, but as a matter of course, the receiving device 4 is not limited to this configuration. FIG. 23 is a block diagram illustrating a configuration of a capsule endoscope system according to a fourth modification of the present embodiment. As illustrated in the capsule endoscope system 1-1 of FIG. 23, a control unit 23-1 of a capsule endoscope 2-1 may include a movement amount acquisition unit 432-1 having a function similar to that of the movement amount acquisition unit 432, and an association unit 433-1 having a function similar to that of the association unit 433. The movement amount acquisition unit 432-1 performs a process similar to the movement amount acquisition process in step S1 of FIG. 6, and the association unit 433-1 performs a process similar to the association process in step S2 of FIG. 6. The control unit 23-1 transmits a wireless signal on which association information from the association unit 433-1 is superimposed together with an image and the like, from the antenna 25 to a receiving device 4-1. In the receiving device 4-1, a image processing unit 43-1 generates a display image on the basis of the association information transmitted from the capsule endoscope 2-1.

FIG. 24 is a block diagram illustrating another configuration of the capsule endoscope system according to the fourth modification of the embodiment. As in the capsule endoscope system 1-2 illustrated in FIG. 24, an image processing unit 52-2 of a processing device 5-2, instead of a receiving device 4-2, may include an image generation unit 431-2 having a function similar to that of the image generation unit 431, the movement amount acquisition unit 432, the association unit 433, and the display image generation unit 434 to display an image in which the first image and the second image are combined, on the display device 6, by display control of a display control unit 54-2, under the control of a control unit 44-2.

In the present embodiment, for convenience of description, the first imaging unit 21A and the second imaging unit 21B alternately performing imaging as illustrated in FIG. 4, and the capsule endoscope 2 moving at a constant speed have been mainly described, but, as a matter of course, the embodiments are not limited thereto. Otherwise, the association unit 433 preferably uses formula (1A) to determine the value of $M_{s(h)}$, applies the determined value of $M_{s(h)}$ to formula (2A), formula (3A), and formula (4A), and determines the first to third conditions. To the formula (1A), a value is applied which is obtained by subtracting the x-coordinate ($L_{1(k)}$) at the position of the first imaging unit 21A upon capturing the first image $G_{1(k)}$, from the x-coordinate ($L_{2(h)}$) at the position of the second imaging unit 21B upon capturing the image $G_{2(h)}$ as the candidate image.

Execution programs for various processing executed in component units of the capsule endoscopes 2 and 2-1, the receiving devices 4, 4-1, and 4-2, and the processing devices 5 and 5-2 of the capsule endoscope systems 1, 1-1, and 1-2 according to the present embodiment may be provided by being recorded in a computer-readable recording medium, such as a CD-ROM, flexible disk (FD), CD-R, DVD, in an installable format file or in an executable format file, or may be provided by being stored on a computer connected to a network such as the Internet, and downloaded via the network. Furthermore, the execution programs may be provided or distributed via the network such as the Internet.

According to some embodiments, two images showing a spatially continuous area between the two images can be associated with each other simply by performing simple processing based on at least an imaging distance in a movement direction of an imaging unit of a capsule endoscope, and a movement amount of the capsule endoscope.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
   a processor comprising hardware, wherein the processor is configured to:
   acquire a movement amount of a capsule endoscope comprising an imaging sensor in a movement direction of the capsule endoscope based on information transmitted from the capsule endoscope;
   determine whether to associate a first image captured by the imaging sensor with a second image captured by the imaging sensor at a time different from a time in which the imaging sensor captures the first image based on an imaging distance of the imaging sensor in the movement direction and the movement amount,
   wherein the imaging distance is a distance between both ends of an effective imaging area along the movement direction in which predetermined brightness and predetermined resolution is provided for an image captured by the imaging sensor; and
   associate the first image with the second image in response to determining to associate the first image with the second image.

2. The image processing apparatus according to claim 1, wherein, in determining whether to associate the first image with the second image, the processor is configured to:
   calculate a first distance along the movement direction between a position of the imaging sensor upon capturing the first image and a position of the imaging sensor upon capturing the second image based on the movement amount;
   compare the first distance and the imaging distance with each other; and
   determine whether to associate the first image with the second image based on a result of the comparison.

3. The image processing apparatus according to claim 2, wherein in comparing the first distance and the imaging distance with each other, the processor is configured to:
   determine whether the first distance is larger than 0 and is not larger than the imaging distance; and
   in response to determining that the first distance is larger than 0 and is not larger than the imaging distance, determine to associate the first image with the second image.

4. The image processing apparatus according to claim 1, wherein in determining whether to associate the first image with the second image, the processor is configured to:
   determine whether there is spatial continuity between the effective imaging area of the imaging sensor upon capturing the first image and the effective imaging area of the imaging sensor upon capturing the second image based on the movement amount; and
   in response to determining that there is the spatial continuity, determine to associate the first image with the second image.

5. The image processing apparatus according to claim 1, wherein the processor is further configured to:
   acquire an angle between an optical axis of the imaging sensor of the capsule endoscope and the movement direction;
   correct the imaging distance of the imaging sensor in the movement direction based on the angle between the optical axis of the imaging sensor and the movement direction to determine a corrected imaging distance; and
   determine whether to associate the first image with the second image based on the corrected imaging distance and the movement amount.

6. The image processing apparatus according to claim 1, wherein the imaging sensor comprises a first imaging sensor and a second imaging sensor, the first imaging sensor having an imaging direction different from an imaging direction of the second imaging sensor, and wherein the first image is an image captured by the first imaging sensor and the second image is an image captured by the second imaging sensor.

7. The image processing apparatus according to claim 1, wherein the processor is further configured to:
   generate a composite image in which the first image and the second image associated with each other are combined; and
   control a display to display the composite image.

8. The image processing apparatus according to claim 7, wherein the processor is configured to:
   divide the second image, associated with the first image, into divided images; and
   generate a composite image in which the divided images are arranged at peripheral edges of the first image.

9. An image processing apparatus comprising:
   a processor comprising hardware, wherein the processor is configured to:
   acquire a movement amount of a capsule endoscope comprising an imaging sensor in a movement direction of the capsule endoscope based on information transmitted from the capsule endoscope; and
   determine whether to associate a first image captured by the imaging sensor with a second image captured by the imaging sensor at a time different from a time in which the imaging sensor captures the first image based on an imaging distance of the imaging sensor in the movement direction and the movement amount, wherein the imaging sensor comprises a first imaging sensor and a second imaging sensor, the first imaging sensor having an imaging direction different from an imaging direction of the second imaging sensor, wherein the first image is an image captured by the first imaging sensor and the second image is an image captured by the second imaging sensor, wherein the imaging distance is the sum of a first observation depth being a distance between both ends of a first effective imaging area along the movement direction in the first effective imaging area of the first imaging sensor, and a second observation depth being a distance between both ends of a second effective imaging area along the movement direction in the second effective imaging area of the second imaging sensor, and wherein the processor is configured to:
calculate a first distance along the movement direction, between a position of the first imaging sensor upon capturing the first image and a position of the second imaging sensor upon capturing the second image, based on the movement amount;
compare the first distance and the imaging distance with each other; and
determine whether to associate the first image with the second image.

10. The image processing apparatus according to claim 9, wherein the processor, in determining whether to associate the first image with the second image, is configured to:
determine that a first condition is satisfied, where the first condition is that the first distance is larger than 0 and is equal to or smaller than the imaging distance;
determine that one of a second condition and a third condition is not satisfied,
where the second condition is that the first distance is equal to or greater than 0 and is less than on equal to the first observation depth, and
wherein the third condition is that the sum of the first distance and the second observation depth is equal to or greater than 0 and is less than or equal to the first observation depth; and
in response to determining that the first condition is satisfied and determining that one of the second condition and the third condition is not satisfied, determine to associate the first image with the second image.

11. An image processing method comprising:
acquiring a movement amount of a capsule endoscope comprising an imaging sensor in a movement direction of the capsule endoscope based on information transmitted from the capsule endoscope;
determining whether to associate a first image captured by the imaging sensor with a second image captured by the imaging sensor at a time different from a time in which the imaging sensor captures the first image based on an imaging distance of the imaging sensor in the movement direction and the movement amount,
wherein the imaging distance is a distance between both ends of an effective imaging area along the movement direction in which predetermined brightness and predetermined resolution is provided for an image captured by the imaging sensor; and
associating the first image with the second image in response to determining to associate the first image with the second image.

12. A non-transitory computer-readable recording medium recording an image processing program causing a computer of an image processing apparatus to at least perform:
acquiring a movement amount of a capsule endoscope comprising an imaging sensor in a movement direction of the capsule endoscope based on information transmitted from the capsule endoscope;
determining whether to associate a first image captured by the imaging sensor with a second image captured by the imaging sensor at a time different from a time in which the imaging sensor captures the first image based on an imaging distance of the imaging sensor in the movement direction and the movement amount,
wherein the imaging distance is a distance between both ends of an effective imaging area along the movement direction in which predetermined brightness and predetermined resolution is provided for an image captured by the imaging sensor; and
associating the first image with the second image in response to determining to associate the first image with the second image.

* * * * *